United States Patent [19]

Wolter et al.

[11] Patent Number: 5,717,125
[45] Date of Patent: Feb. 10, 1998

[54] HYDROLYZABLE AND POLYMERIZABLE SILANES

[75] Inventors: Herbert Wolter, Grossrinderfeld; Werner Storch, Wuerzburg, both of Germany

[73] Assignee: Fraunhofer-Gesellschaft Zur Forderung Der Angewandten, Munich, Germany

[21] Appl. No.: 439,204

[22] Filed: May 11, 1995

[30] Foreign Application Priority Data

May 13, 1994 [DE] Germany ............... 44 16 857.8

[51] Int. Cl.$^6$ ............... C07F 7/08; C07F 7/18; C07F 7/10
[52] U.S. Cl. ............ 556/438; 556/413; 556/418; 556/419; 556/420; 556/427; 556/432; 556/440; 556/449
[58] Field of Search ............... 556/438, 413, 556/418, 419, 420, 427, 437, 440, 449

[56] References Cited

U.S. PATENT DOCUMENTS 5,487,948  1/1996  Stein ............... 556/438 X
5,510,442  4/1996  Bambury et al. ............... 556/438 X

*Primary Examiner*—Paul F. Shaver
*Attorney, Agent, or Firm*—Michael J. Striker

[57] ABSTRACT

The invention includes hydrolyzable and polymerizable silanes, methods of making them and using them to obtain silicic acid(hetero)polycondensates and silicic acid(hetero) polymerizates. The hydrolyzable and polymerizable silanes have the formula I, $$B\{A-(Z)_d-R^1-R'-SiX_aR_b\}_c \quad (I)$$
$$\phantom{B\{A-(Z)_d-}|\phantom{R^1-R'-SiX_aR_b\}_c}$$
$$\phantom{B\{A-(Z)_d-}R^2$$

wherein

A=O, S, NH or C(O)O;

wherein

B=a straight chain or branched organic residue with at least one C=C double bond and from 4 to 50 carbon atoms;

R is an alkyl group, alkenyl group, aryl group, alkylaryl group or an arylalkyl group;

R' is a substituted or unsubstituted alkylene group, arylene group, arylenealkylene group or alkylenearylene group each having zero to ten carbon atoms, with the proviso that the substituted groups each have at least one oxygen atom, sulfur atom and/or amine group substituent;

$R^1$ represents nitrogen, a substituted or unsubstituted alkylene, arylene and alkylenearylene group each having from 1 to 10 carbon atoms, wherein said substituted alkylene groups, arylene groups and alkylenearylene groups each have at least one oxygen atom, sulfur atom and/or amine group substitutent;

X represents hydrogen, halogen, a hydroxy group, an alkoxy group, acyloxy group, alkylcarbonyl group, alkoxycarbonyl group or $-NR''_2$;

R'' is H, alkyl or aryl;

Z=CO or CHR$^4$, wherein R$^4$ is H, alkyl, aryl or alkylaryl; and wherein a=1, 2 or 3;

b=0, 1 or 2;

with the proviso that a+b necessarily=3; and c=1, 2, 3 or 4; and d=0 or 1.

21 Claims, No Drawings

HYDROLYZABLE AND POLYMERIZABLE SILANES

BACKGROUND OF THE INVENTION

The present invention relates to hydrolyzable and polymerizable silanes, methods of making them and methods of using them to make silicic acid polycondensates and/or -heteropolycondensates and polymerizates and/or heteropolymerizates.

Hydrolyzable, organically modified silanes have various applications in the manufacture of scratch-resistant coatings for different substrates, for making filling materials, adhesive and sealing materials or molded bodies. In those applications the silanes, either alone or in mixtures with each other or in the presence of additional hydrolyzable and/or condensable components, are hydrolytically condensed. The final hardening occurs thermally, photochemically, covalent-nucleophilically or is redox induced.

Thus scratch resistant coatings which are described in German Patent DE 3407087 C2 are formed by hydrolytic condensation and comprise, e.g., a hydrolyzable titanium or zirconium compound and a hydrolyzable, organo-functional silane

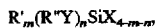

wherein R' represents, e.g., alkyl or alkenyl, R" represents, e.g., alkylene or alkenylene, and X represents a hydrolyzable group.

Adhesive and sealing materials are described in German Patent DE 3536716 A1 which could be obtained by hydrolytic condensation of one or more organosilanes of the general formula $R_mSiX_{4-m}$ and, as needed, one or more of the components $SiX_4$ and/or $R_n(R"Y)_pSiX_{4-n-p}$, wherein R and R" are independently, e.g., an alkyl group, alkenyl group, aryl group, alkylaryl group or an arylalkyl group; X is hydrogen, halogen, a hydroxy group, an alkoxy group or acyloxy group; and Y is a halogen or an unsubstituted or substituted amino, amide, aldehyde, alkylcarbonyl, carboxy, hydroxy, mercapto or cyano group.

Commercial silanes with reactive double bonds are known, such as (meth)acryloxysilanes of the following formula:

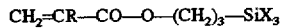

wherein R is hydrogen or methyl and X is, e.g., halogen or alkoxy. These silanes are hydrolyzable and polymerizable and can be used for manufacture of the above-described systems. They offer the great advantage that the resultant coating, the resultant filling material, adhesive material, sealing material or the resultant molded body can be hardened thermally, photochemically, covalent-nucleophilically or can be redox induced by polymerization at the reactive double bond.

Commercial silanes with reactive double bonds, such as the above-described (meth)acryloxysilanes, are in general monofunctional compounds with one C=C double bond and are comparatively low molecular weight and thus comparatively volatile compounds prior to the Si—X hydrolysis and condensation, which are toxicologically hazardous because of the acryl group present. During further processing by polymerization or by modifying functional groups these silanes also have the disadvantage that only chain polymers can be obtained because of the presence of only one reactive double bond and in the above-mentioned modification of functional groups these C=C double bonds required for the organic polymerization are usually lost. Furthermore only one short chain is usually found between the double bonds and the silicon enabling the formation of an inorganic network, so that the mechanical properties (flexibility etc) are only changeable to a limited extent by the organic groups.

Of course hydrolyzable and polymerizable silanes, which provide more than one reactive C=C double bond, are described in German Patent 4011044 C2, and in which the spacing between the reactive double bond and the silicon enabling the formation of the inorganic network is comparatively longer, although still in need of improvement. Also improvement in the functional groups of the molecule would be desirable.

SUMMARY OF THE INVENTION

It is an object of the present invention to provide new organically modified silanes, which are hydrolyzable and polymerizable, which alone, in mixtures or together with other hydrolyzable, condensable or polymerizable components can be used to make scratch-resistant coatings, filling materials, adhesive materials or sealing materials, molded bodies and embedded materials.

It is another object of the present invention to provide new organically modified silanes of the above-described type which are universally usable, which can be built into an inorganic-organic compound system, i.e. into an inorganic-organic network.

It is an additional object of the present invention to provide new organically modified silanes of the above-described type which can be made easily and rapidly, i.e. without expensive syntheses processes.

It is a further object of the present invention to provide new organically modified silanes of the above-described type in which a number of double bonds are provided and the spacing between silicon and the reactive double bonds is adjustable arbitrarily and in which the chain between the silicon and the reactive double bond is provided with hydroxyl or carboxyl functional groups as needed.

These objects and others are attained according to the invention by the hydrolyzable and polymerizable silanes of the formula I,

wherein
a=1, 2 or 3;
b=0, 1 or 2;
with the proviso that a+b necessarily=3; and
c=1, 2, 3 or 4;
wherein
B=a straight chain or branched organic residue having at least one C=C double bond and having 4 to 50 carbon atoms;
X represents a member selected from the group consisting of hydrogen, halogen, hydroxy groups, alkoxy groups, acyloxy groups, alkylcarbonyl groups, alkoxycarbonyl groups and —NR"$_2$;
R" represents a member selected from the group consisting of hydrogen, alkyl groups and aryl groups;
R represents a member selected from the group consisting of alkyl groups, alkenyl groups, aryl groups, alkylaryl groups and arylalkyl groups;
R' represents a member selected from the group consisting of substituted and unsubstituted alkylene groups, arylene groups, arylenealkylene groups and alkylenearylene groups each having from zero to ten carbon atoms, wherein the substituted alkylene groups, the substituted arylene groups, the substituted arylenealkylene groups and the substituted alkylenearylene groups each have at least one oxygen atom, sulfur atom and/or amine group substituent;

$R^1$ is a member of the group consisting of nitrogen, substituted and unsubstituted alkylene, arylene and alkylenearylene groups each having from 1 to 10 carbon atoms, wherein the substituted alkylene groups, the substituted arylene groups and the substituted alkylenearylene groups each have at least one oxygen atom, sulfur atom and/or amine group substitutent;

$R^2$ is a member selected from the group consisting of H, OH and COOH; and wherein, when d=1, Z=CO, the $R^1$ is a substituted or unsubstituted alkylene, arylene or alkylenearylene groups having from 1 to 10 carbon atoms, and $R^2$ is either H or COOH, then A is either an oxygen atom, a sulfur atom or an NH group; and wherein, when d=1, Z=CHW and W represents a member selected from the group consisting of H, alkyl groups, aryl groups and alkyaryl groups, and the $R^1$ is a substituted or unsubstituted alkylene, arylene or alkylenearylene groups having from 1 to 10 carbon atoms, and $R^2$ is OH, then A is either an oxygen atom, a sulfur atom, an NH group or a COO group; and wherein, when d=0 and $R^1$ is a substituted or unsubstituted alkylene groups, arylene groups or alkylenearylene groups having from 1 to 10 carbon atoms and $R^2$ is OH, then A is O, S, NH or COO; and wherein when d=1, Z=CO, $R^1$=N and $R^2$=H, then A is S.

The silanes of formula I are polymerizable by the B group and hydrolyzable by the X group. An inorganic network with Si—O—Si bonds can be built up by the hydrolyzable groups, while the double bonds in the B group can be polymerized to build up an organic network.

The alkyl groups above are, e.g., straight chain, branched or cyclic groups with from 1 to 20 carbon atoms, particularly with 1 to 10 carbon atoms, and advantageously are lower alkyl groups with from 1 to 6 carbon atoms, especially with 1 to 4 carbon atoms. Particular examples of appropriate alkyl groups include methyl, ethyl, n-propyl, i-propyl, n-butyl, i-butyl, s-butyl, t-butyl, n-pentyl, n-hexyl, cyclohexyl, 2-ethylhexyl, dodecyl and octadecyl groups.

The alkenyl groups are, e.g., straight chain, branched or cyclic groups with from 2 to 20, advantageously from 2 to 10, carbon atoms and advantageously lower alkenyl groups with from 2 to 6 carbon atoms, such as vinyl, allyl and 2-butenyl.

Preferred aryl groups include phenyl, biphenyl and naphthyl groups. The alkoxy, acyloxy, alkylamino, dialkylamino, alkylcarbonyl, alkoxycarbonyl, arylalkyl, alkylaryl, alkylene and alkylenearylene groups are advantageously derived from the above-described alkyl and aryl groups. Special examples are methoxy, ethoxy, n- and i-propoxy, n- , i- , s- and t-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-named groups can have one or more substituents as needed, e.g. halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, isocyanato, nitro, epoxy, $SO_3H$ and $PO_4H_2$.

Fluorine, chlorine and bromine are particularly preferred halogens. Chlorine is especially preferred.

For a≧2 and/or b=2 the X and R groups are the same or different.

The group B derives itself from a substituted or unsubstituted compound $B(AH)_c$, has at least one C=C double bond and is e.g. a vinyl, an allyl, an acryl or a methacryl group. The group B has from 4 to 50 carbon atoms, advantageously 6 to 30 carbon atoms. Advantageously B is derived from a substituted or unsubstituted compound with at least two acrylate or methacrylate groups. Compounds of this type are designated as (meth)acrylate. In cases in which the compound $B(AH)_c$ is substituted, the substituents can be as described above. The group —AH can be —OH, —SH, —$NH_2$ or —COOH and c can take values of from 1 to 4.

Without limitation the following are concrete examples of the B group:

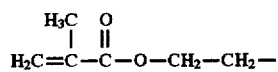

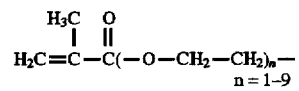

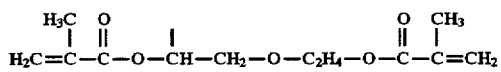

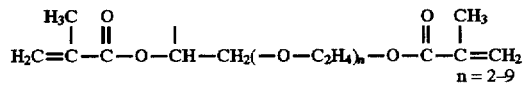

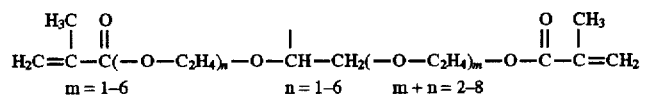

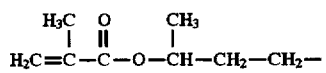

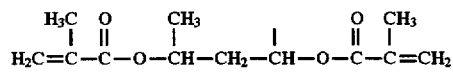

-continued
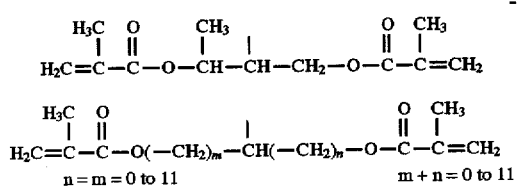
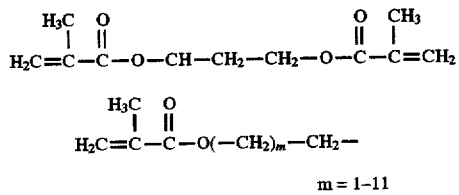
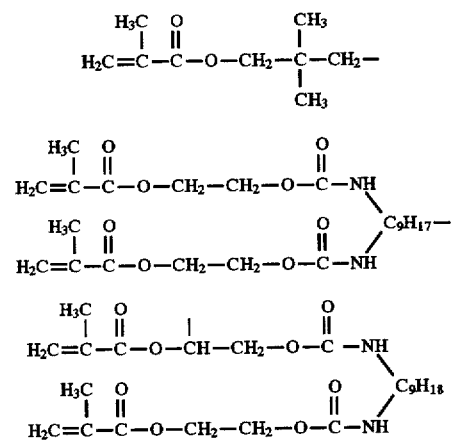
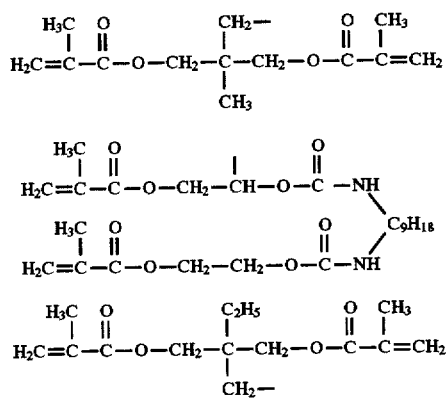
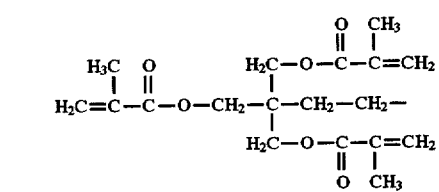
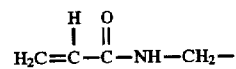
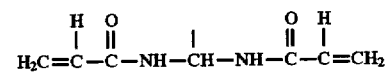
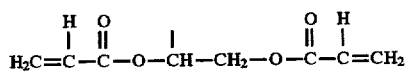
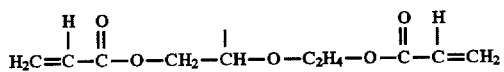
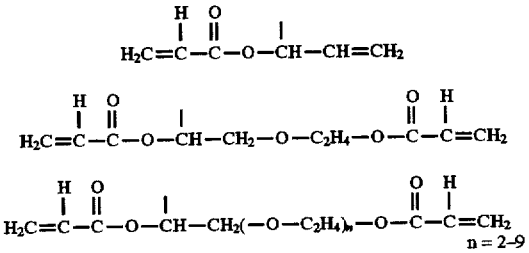
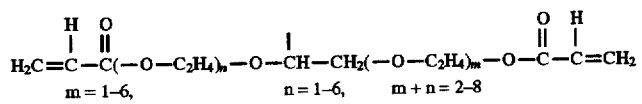
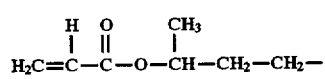
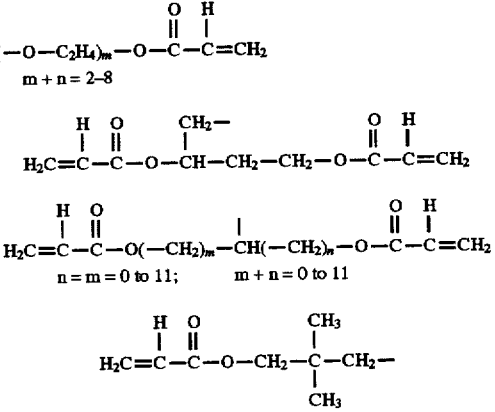
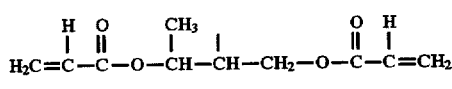
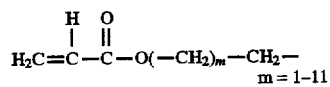
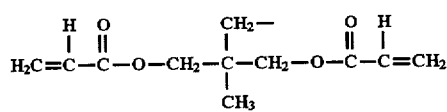
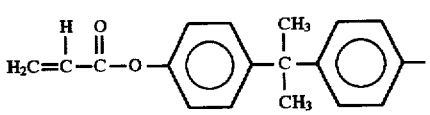

7
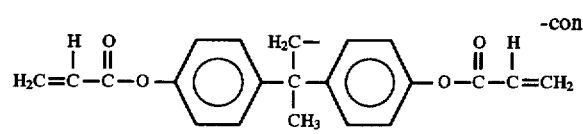
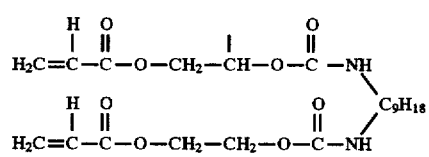
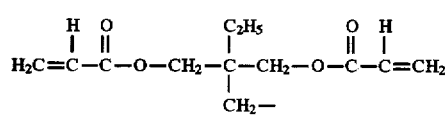
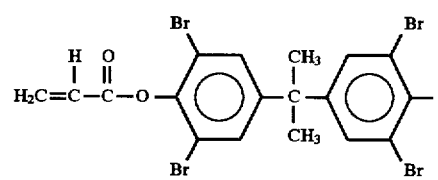
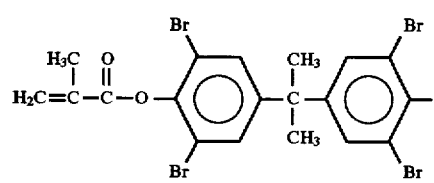
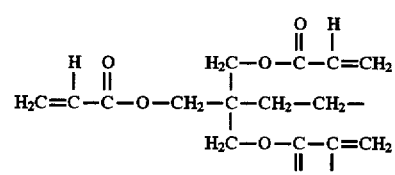
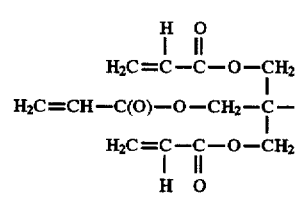
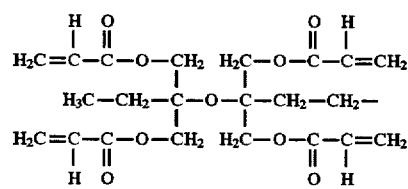
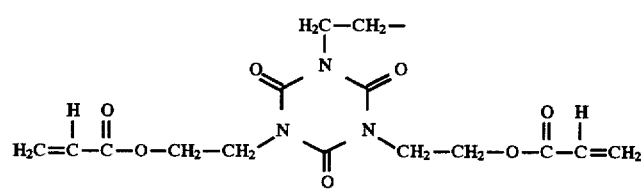
8
-continued
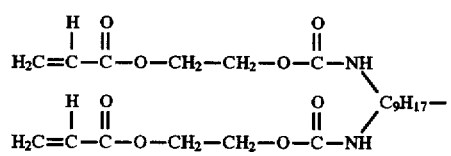
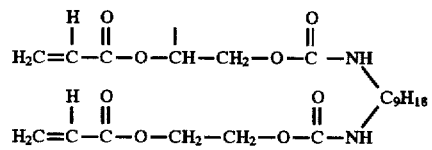
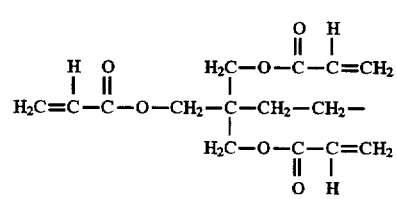
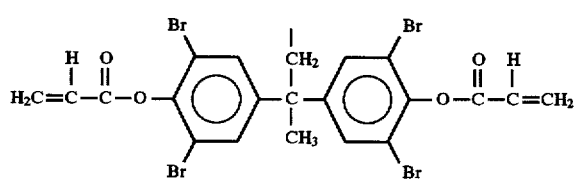
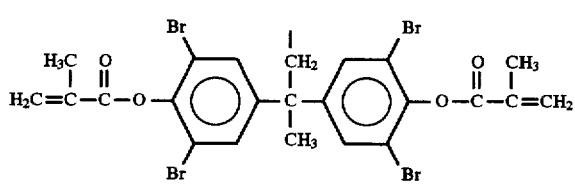
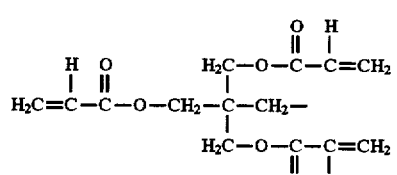
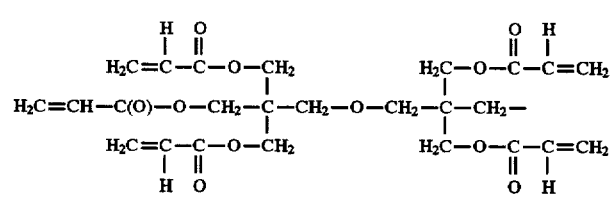
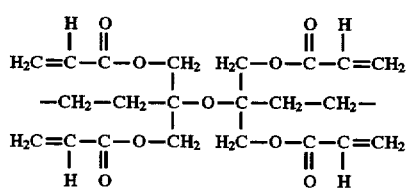

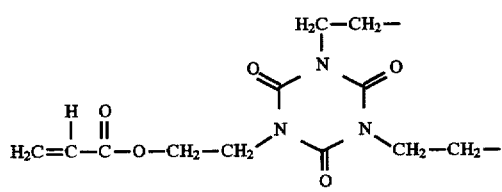
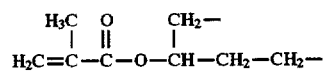
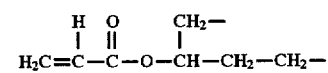
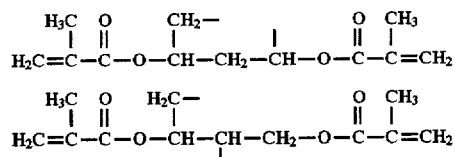
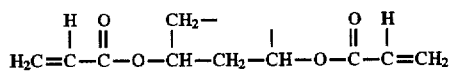
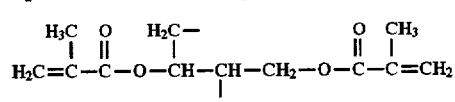
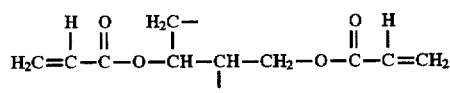
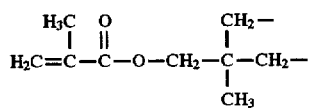
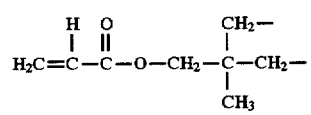
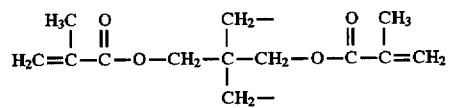
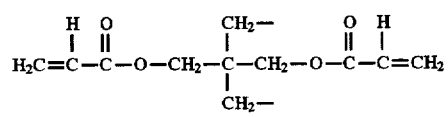
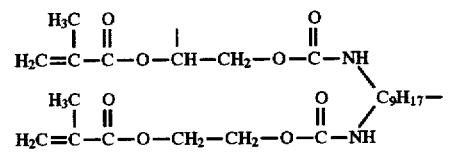
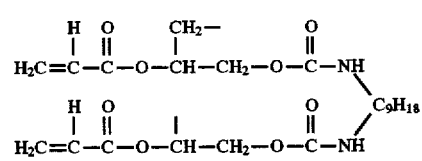
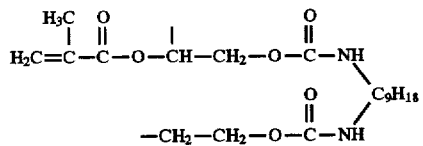
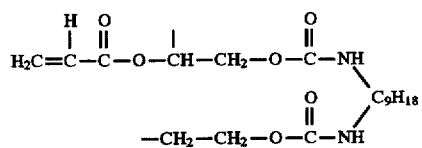
 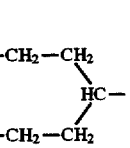
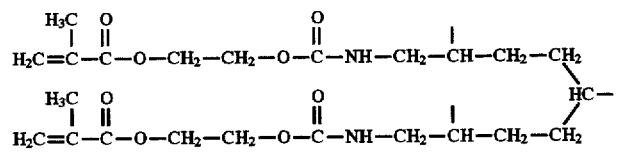
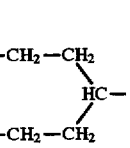
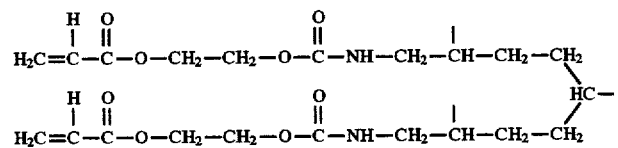
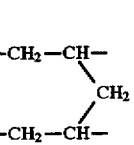
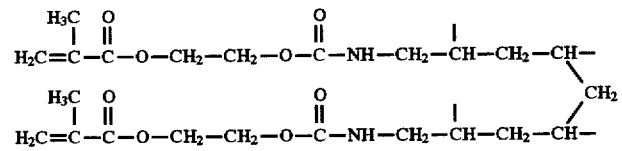
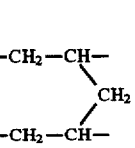
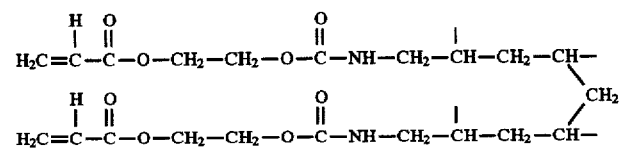

-continued
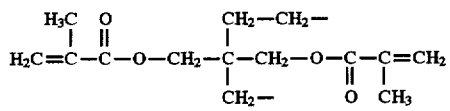
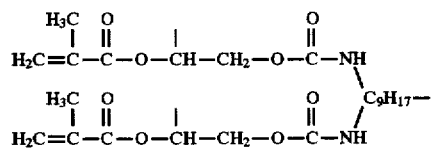
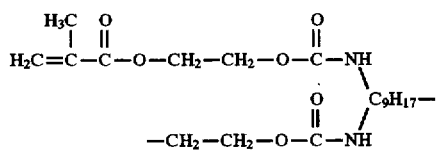
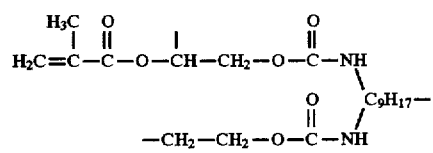
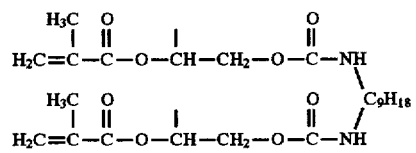
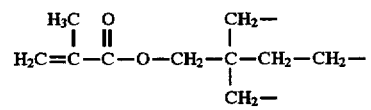
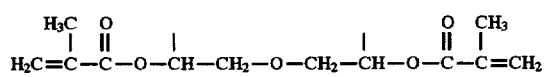
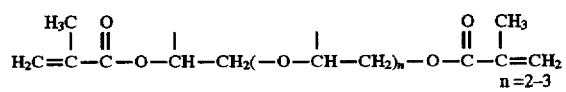
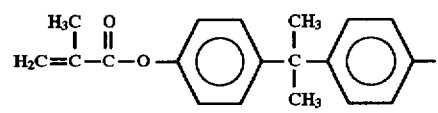
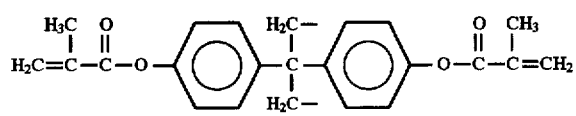
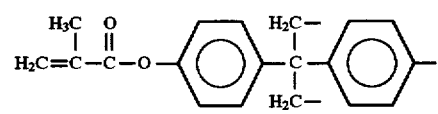
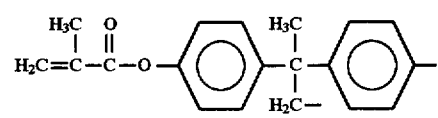
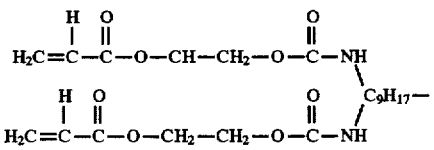
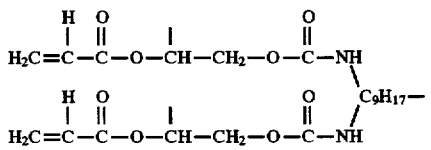
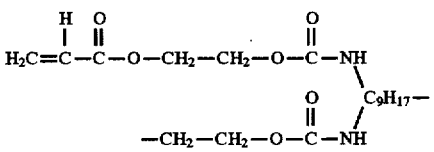
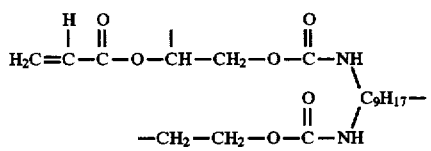
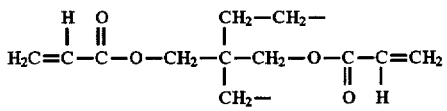
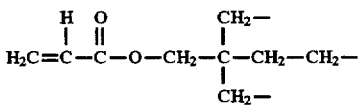
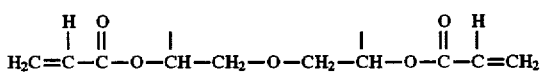
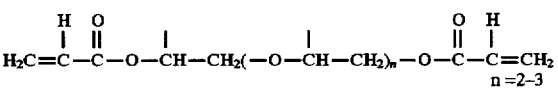
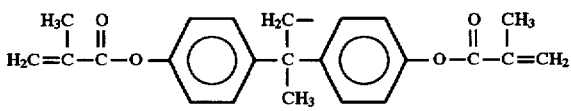
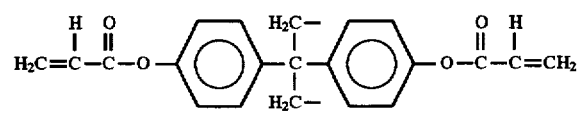
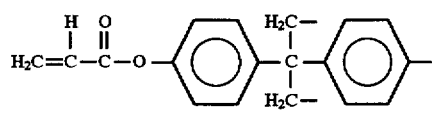
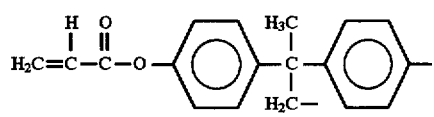

-continued
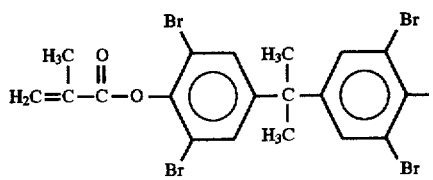
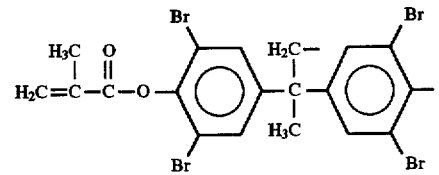
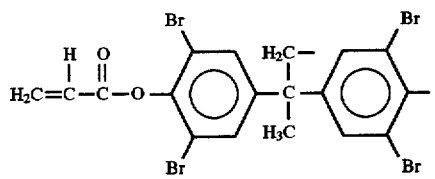
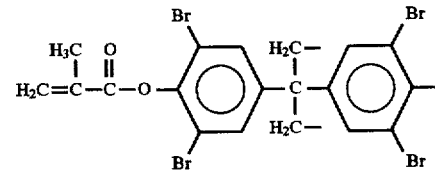
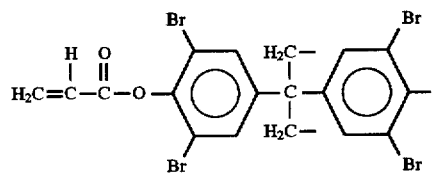
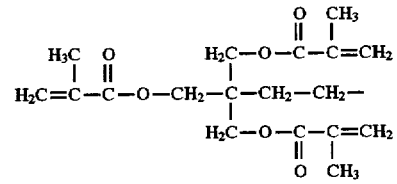
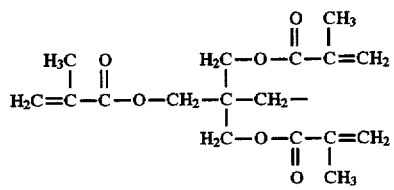
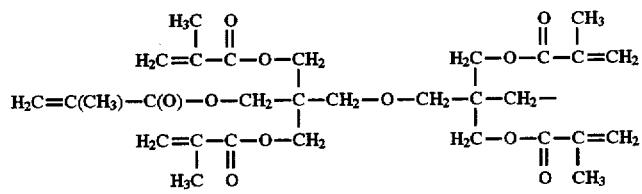
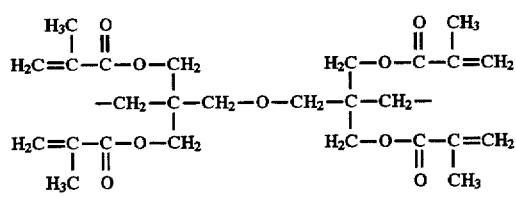
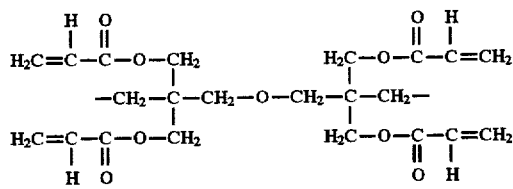
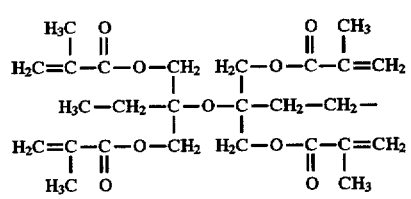
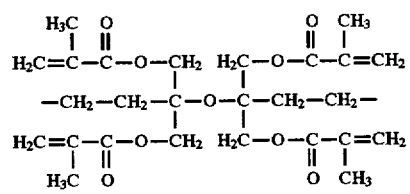
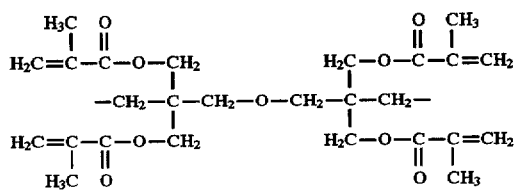
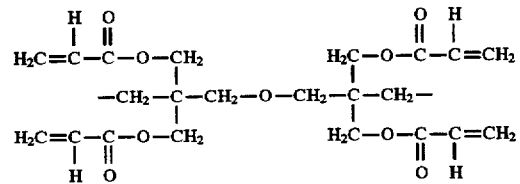

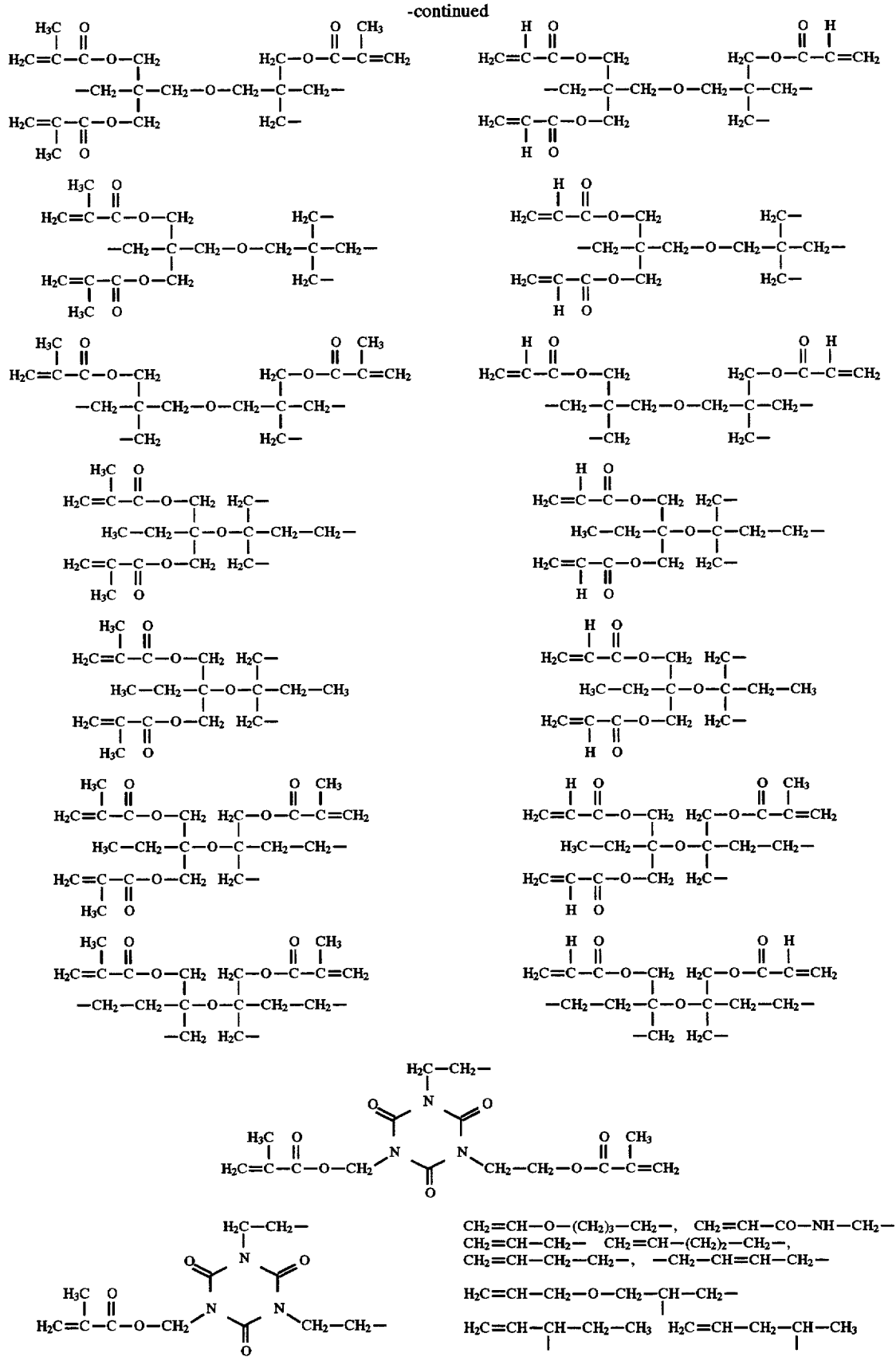

-continued

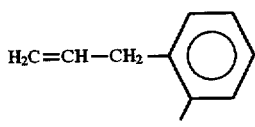
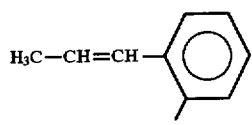
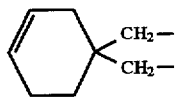
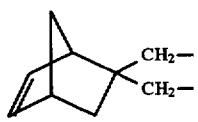
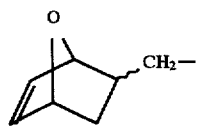

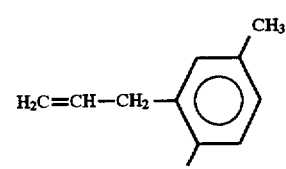
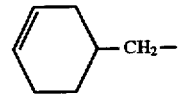
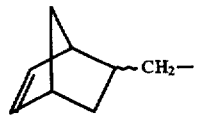
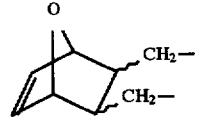
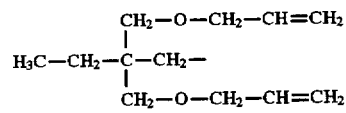

The group B can be coupled by its free valences with another group —A(Z)$_d$— which can have the following form:

—O—CO—, —S—CO—, —NH—CO—, —O—CH$_2$—, —O—CHR—, —S—CH$_2$—, —S—CHR—, —NH—CH$_2$—, —NH—CHR—, —CO—O—CH$_2$—, —CO—O—CHR—, —O—, —S—, —NH— and —CO—O—, wherein R=alkyl, aryl or alkylaryl.

The alkyl groups are straight chain, branched or cyclic groups having from 1 to 20 carbon atoms, especially from 1 to 10 carbon atoms, and advantageously lower alkyl groups having from 1 to 6 carbon atoms. Alkyl groups having 1 to 4 carbon atoms are especially preferred. Particular examples of preferred alkyl groups include methyl, ethyl, n-propyl, i-propyl, n-butyl, i-butyl, s-butyl, t-butyl, n-pentyl, n-hexyl, cyclohexyl, 2-ethylhexyl, dodecyl and octadecyl groups. Advantageous aryl groups include phenyl, biphenyl and naphthyl groups.

The silanes according to the invention can be made by the following methods.

Type a) This method of making the hydrolyzable and polymerizable silanes of formula I comprises performing an addition reaction of B(AH)$_c$ to a cyclic carboxylic acid anhydride of the formula II:

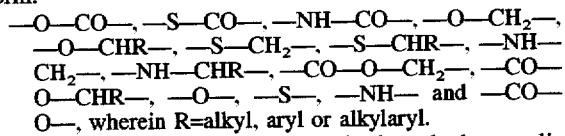
(II)

wherein R$^1$ is an alkylene, arylene or alkylarylene group and X, B, R, R', a, b, a+b and c are as defined hereinabove in relation to formula I. Also A is an O atom, a S atom or an NH group.

Type b) This method for making the hydrolyzable and polymerizable silanes of formula I as defined above comprises performing a condensation reaction of B(AH)$_c$ with a carboxylic acid of the formula III:

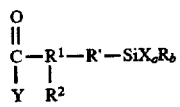
(III)

wherein Y is selected from the group consisting of Cl, OH and OR* and wherein R* and R$^1$ are each independently an alkylene or an alkylenearylene, and the B, R, R', a, b, a+b, c and X groups are as defined hereinabove in connection with the silanes of formula I.

Type c) This method for making the hydrolyzable and polymerizable silanes of formula I above comprises performing an addition reaction of B(AH)$_c$ with a substituted epoxide selected from the group consisting of the epoxides of formula IV and epoxides of formula IX:

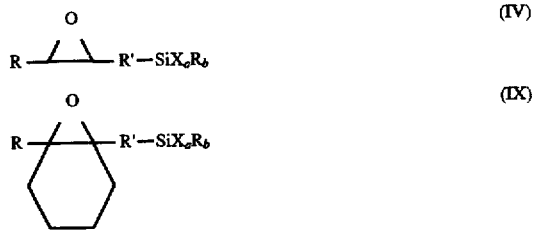
(IV)

(IX)

wherein A is an oxygen atom, a sulfur atom, an NH group or a COO group, and the B, X, R, R', a, b, a+b and c are as defined in claim 1.

Type d) The type d) method for making the hydrolyzable and polymerizable silane of the formula I comprises performing an addition reaction of B(AH)$_c$ with a substituted silane of the formula V OCN—R'—SiX$_a$R$_b$    (V)

wherein A is sulfur and B, R, R', a, b, c and X are as defined in relation to the silanes of formula I.

Concrete examples of the adduct, B(AH)c, with c=1 to 4 result, when the free valences of the concrete examples for the B group of the foregoing pages are saturated with AH groups, where AH equal OH, SH, NH$_2$ or COOH.

In the following pages detailed concrete reaction equations illustrating in more detail the above methods for synthesizing hydrolyzable and polymerizable silanes are provided.

Type a) (with B(AH)$_c$=BOH)

Analogous reactions for B(AH)$_c$=B(OH)$_c$, B(SH)$_c$ and B(NH$_2$)$_c$ are possible, with c=1 to 4. In general:

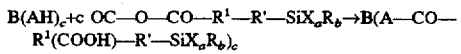

Type b) (with B(AH)$_c$=BOH and Y—CO—=Cl—CO—)

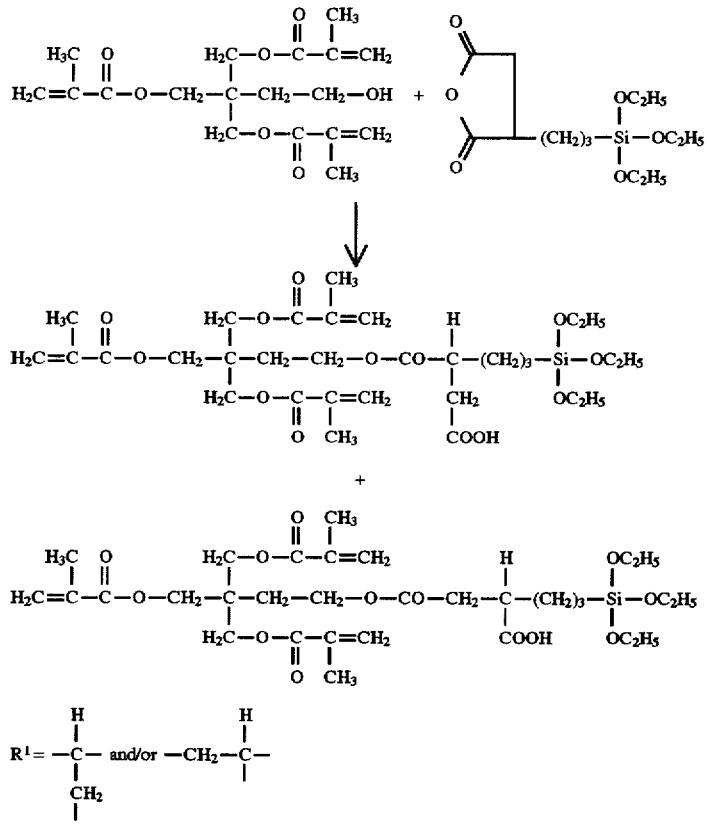

—A—=—O—, —Z—=—CO—, —R$^2$=—COOH, —R'—=—(CH$_2$)$_3$—, —X=—OC$_2$H$_5$, a=3, b=0, c=1 and d=1

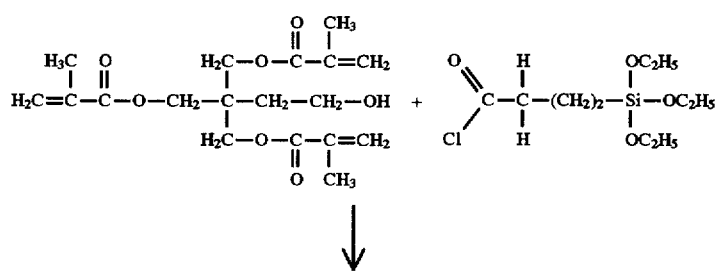

-continued
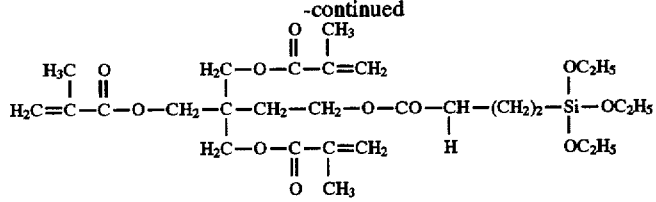
Analogous reactions are possible for $B(AH)_c=B(OH)_c$, $B(SH)_c$, $B(COOH)_c$ and $B(NH_2)_c$, with $c=1$ to 4. In general:
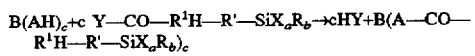
Type c) (with $B(AH)_c=BOH$)
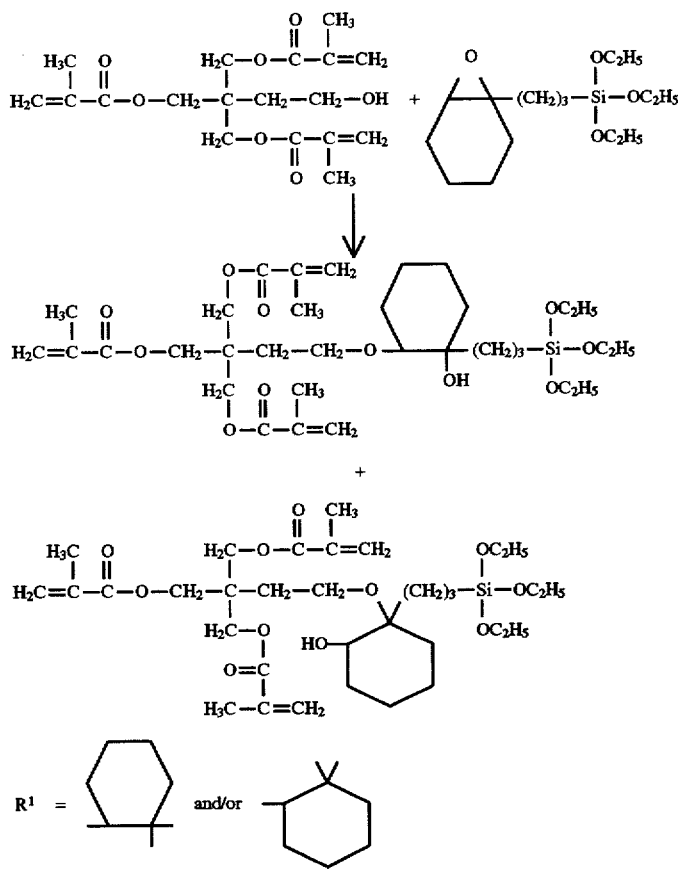
$-A-=-O-$, $-R^2=-OH$, $-R'-=-(CH_2)_3-$, $-X=-OC_2H_5$, $a=3$, $b=0$, $c=1$ and $d=0$.

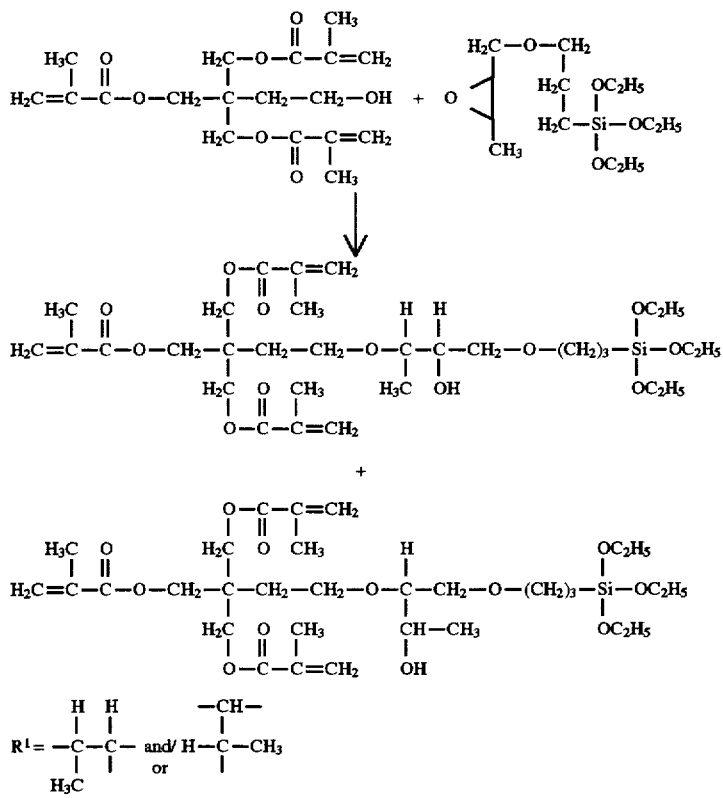

$-A- = -O-, -R^2 = -OH, -R'- = -CH_2-O-(CH_2)_3-, -X = -OC_2H_5,$
$a = 3, b = 0, c = 1, d = 0.$

Analogous reactions are possible for $B(AH)_c=B(OH)_c$, $B(SH)_c$, $B(COOH)_c$ and $B(NH_2)_c$, with $c=1$ to 4. In general:

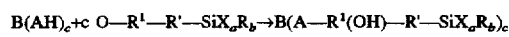

Type d) (with $B(AH)_c=BSH$)

With all 4 reaction types a) to d) a plurality, up to four, addition products of the corresponding silanes with the compound $B(AH)_c$, with $c=2, 3$ or 4, are possible.

Concrete examples of the $-R'-SiX_aR_b$ group are as follows without limitation:

$-(CH_2)_n-Si(CH_3)_2(OC_2H_5)$, with $n=0$ to 10

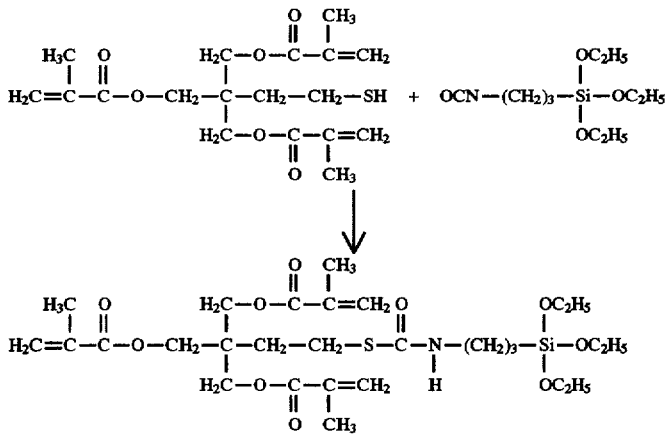

$-A- = -S-, -Z- = -CO-, R^1 = N, -R^2 = -H, -R'- =$
$-(CH_2)_3-, -X = -OC_2H_5, a = 3, b = 0, c = 1$ and $d = 1$.

Analogous reactions are possible for $B(AH)_c=B(SH)_c$, with $c=1$ to 4. In general:

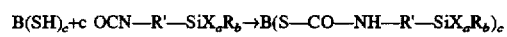

$-(CH_2)_n-Si(CH_3)(OC_2H_5)_2$, with $n=0$ to 10
$-(CH_2)_n-Si(OC_2H_5)_3$, with $n=0$ to 10
$-(CH_2)_n-Si(C_2H_5)_2(OCH_3)$, with $n=0$ to 10

—(CH$_2$)$_n$—Si(C$_2$H$_5$)(OCH$_3$)$_2$, with n=0 to 10
—(CH$_2$)$_n$—Si(OCH$_3$)$_3$, with n=0 to 10
—(CH$_2$)$_n$—Si(CH$_3$)$_2$(OCH$_3$), with n=0 to 10
—(CH$_2$)$_n$—Si(CH$_3$)(OCH$_3$)$_2$, with n=0 to 10
—(CH$_2$)$_n$—Si(C$_2$H$_5$)$_2$(OC$_2$H$_5$), with n=0 to 10
—(CH$_2$)$_n$—Si(C$_2$H$_5$)(OC$_2$H$_5$)$_2$, with n=0 to 10
—(CH$_2$)$_n$—Si(CH$_3$)(C$_2$H$_5$)(OCH$_3$), with n=0 to 10
—(CH$_2$)$_n$—Si(CH$_3$)(C$_2$H$_5$)(OC$_2$H$_5$), with n=0 to 10
—(CH$_2$)$_n$—Si(CH$_3$)(OC$_2$H$_5$)(OCH$_3$), with n=0 to 10
—(CH$_2$)$_n$—Si(C$_2$H$_5$)(OC$_2$H$_5$)(OCH$_3$), with n=0 to 10
—(CH$_2$)$_n$—Si(OC$_2$H$_5$)$_2$(OCH$_3$), with n=0 to 10
—(CH$_2$)$_n$—Si(OC$_2$H$_5$)(OCH$_3$)$_2$, with n=0 to 10
—(CH$_2$)$_n$—Si(CH$_3$)(OC(CH$_3$)=CH$_2$)$_2$, with n=0 to 10
—(CH$_2$)$_n$—Si(C$_2$H$_5$)(OC(CH$_3$)=CH$_2$)$_2$, with n=0 to 10
—(CH$_2$)$_n$—Si(CH$_3$)$_2$(OC(CH$_3$)=CH$_2$), with n=0 to 10
—(CH$_2$)$_n$—Si(C$_2$H$_5$)$_2$(OC(CH$_3$)=CH$_2$), with n=0 to 10
—(CH$_2$)$_n$—Si(OCH$_3$)(OC(CH$_3$)=CH$_2$)$_2$, with n=0 to 10
—(CH$_2$)$_n$—Si(OC$_2$H$_5$)(OC(CH$_3$)=CH$_2$)$_2$, with n=0 to 10
—(CH$_2$)$_n$—Si(OCH$_3$)$_2$(OC(CH$_3$)=CH$_2$), with n=0 to 10
—(CH$_2$)$_n$—Si(OC$_2$H$_5$)$_2$(OC(CH$_3$)=CH$_2$), with n=0 to 10
—(CH$_2$)$_n$—Si(C$_6$H$_5$)(OC$_2$H$_5$)$_2$, with n=0 to 10
—(CH$_2$)$_n$—Si(C$_6$H$_5$)(OCH$_3$)$_2$, with n=0 to 10
—(CH$_2$)$_n$—Si(C$_6$H$_5$)(OCH$_3$)(OC$_2$H$_5$) with n=0 to 10
—(CH$_2$)$_n$—Si(C$_6$H$_5$)(OC(CH$_3$)=CH$_2$)$_2$, with n=0 to 10

The silanes according to the invention, which are obtained by the manufacturing process according to type a), have one or more carboxyl groups (—R$^2$=—COOH) in the portion of the silane molecule between the silicon atom and the B group. These carboxyl groups have a certain definite effect on the molecular properties and allow their further modification. The carboxyl groups function as charge carriers, which makes the use of the silanes according to the invention in dispersions and/or emulsion or in electric immersion coating very advantageous. Furthermore the carboxyl groups provide acid catalysis, e.g. during a sol-gel process, which has the significant advantage that the following separation steps, namely the separation of the catalyst compounds, are eliminated. Further the carboxyl groups increase the water solubility of the silanes according to the invention so that they can be used in water-based paints. Furthermore the carboxyl groups act as bonding groups for inorganic and organic surfaces. Also the carboxyl groups have the ability to complex titanium, zirconium, tin and other metals, which has a particularly positive effect on the X-ray opacity, the contact oxidation and the increase in the index of refraction. Further the carboxyl and hydroxyl groups (Type c, —R$^2$=—OH) can be used for providing additional functional groups by addition of other organic molecules, e.g. for RNCO or RCOCl.

Particularly applications in the dental field (e.g. bonding agents) are provided by the combination of a carboxyl group with a polymerizable C=C double bond and a silicon portion and by the resulting possibility of bonding to, e.g., zirconium (to provide X-ray opacity). The bonding action may be further increased by combination with a silane anhydride.

The combination of the carboxyl groups with polymerizable C=C double bonds in connection with the inorganic silane portion produces an ideal compound for use as a polyalkene carboxylic acid in ionomer cements.

When an amino-olefin (B(NH$_2$)$_c$) is used in the Type a) manufacturing process, the carboxyl groups can react with the amide groups to form an imide structure and disappear during a thermal hardening (polymerization of the C=C double bonds). This has the consequence that an additional hardening mechanism besides the double bond polymerization is provided by intermolecular reactions and that the carboxyl groups which are troublesome for certain applications are eliminated in the hardened state. An amide and/or amine-containing additive is required in other nonamine-containing systems.

The silanes according to the invention are stable compounds and can be processed further, either alone or together with other hydrolyzable, condensable and/or polymerizable components to form silicic acid polycondensates or silicic acid heteropolycondensates, whose final hardening can take place then by polymerization of the C=C double bonds. The silanes according to the invention can be further processed, alone or together with other hydrolyzable, condensable and/or polymerizable components, to obtain polymerizates, which can be solidified or condensed by subsequent hydrolytic condensation.

Silicic acid heteropolycondensates, which are modified with organic groups, and processed for their manufacture (e.g. based on hydrolytically condensable organosilanes according to a sol-gel process) are known in great number. This type of condensate is useful, as mentioned above, for different purposes, e.g. as mold bodies, in coatings, etc. Because of the large number of applications for this class of substance, there is a continuing need for modification of the already known condensates, on the one hand because new applications open up and on the other hand to optimize the properties of existing applications.

The silanes according to the invention are hydrolyzable and condensable in basic or acidic media, or alternatively because the C=C double bonds react or join together. Because of that it is possible to build the silanes according to the invention into an inorganic-organic network by hydrolytic condensation. The silanes according to the invention contain hydrolyzable groups X, e.g. alkoxy groups, so that an inorganic network (Si—O—Si bonds) can be built up, while the C=C double bonds contained in the B groups can be polymerized to form an organic network. Because of that it is possible to replace the organically modified hydrolyzable and condensable silanes according to the state of the art in coatings, filling materials, adhesive and sealing materials and in mold bodies and embedded materials with silanes according to the invention.

The silanes according to the invention, using co-condensable components as needed, are hydrolyzed and polycondensed to form an inorganic network. The polycondensation occurs advantageously according to the sol-gel process, as is described, for example, in German Patent Documents DE-A1 2758414, 2758415, 3011761, 3826715 and 3835968.

The silanes according to the invention, together with other copolymerizable components as needed, are polymerized to form an organic network. The polymerization can occur, e.g. thermally, in a redox induced manner, covalent-nucleophilically and/or photochemically using methods described, e.g. in German Patent Documents DE-A1 3143820, 3826715 and 3835968.

Compounds, which are polymerizable radically and/or ionically, can be used as additional polymerizable components. Radically polymerizable compounds, which can be used, include those with C=C double bonds, such as acrylate or methacrylate for which the polymerization occurs by the C=C double bonds. Ionically polymerizable compounds which can be used include, e.g., ring systems, which are polymerizable by cationic ring opening, such as spiroorthoester, spiroorthocarbonate, bicyclic spiroorthoester and mono- or oligoepoxides. However compounds, which are both ionically and also radically polymerizable, can be used, such as methacryloyl-spiroorthoester. These compounds are radically polymerizable via the C=C double bond and cationically polymerizable via ring opening. The making of these systems is, for example, described in the Journal f. prakt. Chemie(Journal for Practical Chemistry), Volume 330, Number 2, 1988, pp. 316–318. Furthermore silanes according to the invention can be used in systems such as described in German Patent 4405261.

Furthermore it is also possible to include other known silane-bound cyclic systems by copolymerization. These systems for example contain the epoxide group. These systems are described in German Patent DE 4125201 C1 in connection with the making of spiro-silanes.

The silanes according to the invention produce highly reactive systems, which lead to polyheterocondensates, which lead, e.g., to mechanically stable coatings or mold bodies and/or filling bodies on UV-irradiation for a very short time. The silanes according to the invention are made by simple addition reactions and can have a variable number of reactive groups of different functionality by suitable selection of the starting compounds.

The formation of a three-dimensional organic network is possible when two or more C=C double bonds are present in the B groups. By appropriate dimensioning of the spacing between the Si atom and the B group, i.e. by selecting chain length, and by the presence of additional functional groups in this chain, the mechanical properties (e.g. flexibility) and the physicochemical properties (adsorption, index of refraction, adherency, etc) of the poly(hetero)condenstates can be controlled. According to the type and number of hydrolyzable groups (alkoxy groups) silicon-type or glass-type properties of the poly(hetero)condensate can be obtained by formation of an inorganic network.

The silanes according to the invention have a comparatively high molecular weight and correspondingly a comparatively low volatility relative to pure methacrylate monomers, so that the danger of toxicity problems during the processing and application of these materials is comparatively minor. Polysiloxanes with still lower volatility, which thus completely eliminate toxicity problems of the acryl components, can be formed by inorganic and/or organic cross-linking.

Considering the possible variations of co-condensable and copolymerizable components already disclosed above, the silicic acid (hetero)polycondensates produced from the silanes according to the invention can be adapted in many ways to various suggested uses, and can be used in all fields in which silicic acid (hetro)polycondensates are already used. Also the silicic acid (hetero)polycondensates produced from the silanes according to the invention provide new applications, e.g. in the fields of optics, electronics, medicine, electrooptics and packaging materials for foods.

The silanes according to the invention can be used either as such or in compositions which contain additional additives adapted for the particular application, e.g. common paint additives, solvents, filling materials, photoinitiators, thermal initiators, flow agents and pigments. The silanes according to the invention or the compositions containing the silanes are appropriate, for example, for making coatings, filling materials or bulk materials, adhesive materials and extrusion materials, fibers, particles, foils, adhesive materials, molded bodies and embedded materials. Coatings and molded bodies made from silanes according to the invention have the advantage that they can be structured photochemically. Special fields of application include, the coating of substrates made from metal, plastic, paper, ceramics, etc. by dipping, pouring, spraying, brushing, electrostatic spraying, electric immersion painting, etc.; the field of optical, electrooptic and electronic components; the manufacture of filling materials, the making of scratch-resistant, wear-resistant corrosion protecting coatings, the making of molded bodies, e.g. by injection molding, casting, pressing, rapid-prototyping or extrusion, and making of composites, e.g. with fibers, filling materials or textiles.

Still other hydrolytic condensable compounds of silicon, of boron, of aluminum, of phosphorus, of tin, of lead, of the transition metals, of lanthanides or actinides can be used together with the silanes according to the invention of formula I. These other hydrolytically condensable compounds can be used to make the polycondensates either as such or in already precondensed form. It is particularly advantageous when at least 10 Mol %, particularly at least 80 Mol-% and especially at least 90 Mol-%, of the starting materials for making silicic acid (hetero)polycondensates are silicon compounds.

Similarly it is advantageous when the silicic acid (hetero) polycondensates are based on at least 5 Mol-%, e.g. 25 to 100 Mol-%, especially 50 to 100 Mol-%, and even more especially from 75 to 100 Mol-%, based on the monomer compounds, of at least one silane according to the invention.

The silicon compounds which can be used as hydrolytically condensable silicon compounds include the silicon compounds of the formula VI

$$R_a(R''Z')_b SiX_{4-(a+b)}$$ (VI)

in an uncondensed or precondensed form, wherein the R, R", X and Z' groups are the same or different and have the following significance:

X represents hydrogen, halogen, a hydroxy group, an alkoxy group, an acyloxy group, an alkylcarbonyl group, an alkoxycarbonyl group and —NR'$_2$, where R' represents hydrogen, an alkyl group or an aryl group;

R represents an alkyl, alkenyl, aryl, alkylaryl or arylalkyl group;

R" is a substituted or unsubstituted alkylene or alkenylene group, wherein these groups can also contain at least one oxygen atom, sulfur atom or —NH group substituent;

Z' is a halogen or a substituted or unsubstituted amine, amide, aldehyde, alkylcarbonyl, carboxyl, mercapto, cyano, alkoxy, alkoxycarbonyl, sulfonic acid, phosphoric acid, acryloxy, methacryloxy, epoxy or vinyl group; and a'=0, 1, 2 or 3 and b'=0, 1, 2 or 3, with a'+b' necessarily=1, 2 or 3.

These silanes are, e.g., described in German Patent Document 34 07 087 C2. The alkyl groups are, e.g., straight chain, branched or cyclic groups with from 1 to 20 carbon atoms, advantageously from 1 to 10 carbon atoms, and especially preferably lower alkyl groups having from 1 to 6 carbon atoms. Special examples include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with 2 to 20 carbon atoms, advantageously from 2 to 10 carbon atoms, and especially preferably lower alkenyl groups from 2 to 6 carbon atoms, such as vinyl, allyl or 2-butenyl groups.

The aryl groups are advantageously phenyl, biphenyl and naphthyl.

The alkoxy-, acyloxy-, alkylcarbonyl-, alkoxycarbonyl- and amino groups are advantageously derived by reaction from the above-described alkyl and aryl groups. Special examples include methoxy, ethoxy, n- and i-propoxy, n, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-mentioned groups can of course have one or more substituents, as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxyl, mercapto, cyano, nitro, epoxy, $SO_3H$ and $PO_4H_2$. The halogens are advantageously fluorine, chlorine and bromine.

Special examples of the hydrolytically condensable silanes of the formula VI are:

$CH_3$—Si—$Cl_3$, $CH_3$—Si—$(OC_2H_5)_3$, $C_2H_5$—Si—$Cl_3$,
$C_2H_5$—Si—$(OC_2H_5)_3$, $CH_2$=CH—Si—$(OC_2H_5)_3$,
$CH_2$=CH—Si—$(OC_2H_4OCH_3)_3$, $(CH_3)_2$—Si—$Cl_2$,
$CH_2$=CH—Si—$(OOCCH_3)_3$, $(CH_3)_2$—Si—$(OC_2H_5)_2$,
$(C_2H_5)_3$—Si—Cl, $(C_2H_5)_2$—Si—$(OC_2H_5)_2$,
$(CH_3)_2(CH_2$=CH)—Si—$Cl_2$, $(CH_3)_3$—Si—Cl,
(t—$C_4H_9$)$(CH_3)_3$—Si—Cl, $(CH_3O)_3$—Si—$C_3H_6$—NH—
$C_2H_4$—NH—$C_2H_4$—$NH_2$, $(CH_3O)_3$—Si—$C_3H_6$—SH,
$(CH_3O)_3$—Si—$C_3H_6$—Cl, $(CH_3O)_3$—Si—$C_3H_6$—NH—
$C_2H_4$—$NH_2$, $(CH_3O)_3$—Si—$C_3H_6$—O—C(O)—C($CH_3$)=$CH_2$,
$(CH_3)_2(CH_2$=CH—$CH_2$)—Si—Cl, $(C_2H_5O)_3$—Si—
$C_3H_6$—$NH_2$, $(C_2H_5O)_3$—Si—$C_3H_6$—CN, $(CH_3O)_3$—Si—$C_3H_6$—O—$CH_2$—[epoxide ring structure]

$(CH_3O)_3$—Si—$(CH_2)_2$—[cyclohexyl epoxide structure]

The silicon compounds which can be used as hydrolytically condensable silicon compounds include the silicon compounds of the formula VII $$\{X_nR_kSi[(R^3A')_l]_{4-(n+k)}\}_xB \quad (VII)$$

in an uncondensed or precondensed form.

The A', R, $R^3$ and X groups can be the same or different and A' is an O, S, PR'", POR'", NHC(O)O or NHC(O)NR'" group, and R'" is hydrogen, an alkyl or an aryl group, X represents hydrogen, halogen, a hydroxy group, an alkoxy group, an acyloxy group, an alkylcarbonyl group, an alkoxycarbonyl group and —NR'$_2$, where R' represents hydrogen, an alkyl group or an aryl group;

B is a straight chain or branched organic residue derived from a starting compound B' having from 5 to 50 carbon atoms and at least one C=C double bond if l=1 and A=NHC(O)O or NHC(O)NR'" but otherwise at least two C=C double bonds, $R^3$ is alkylene, arylene or alkylenearylene, R represents an alkyl, alkenyl, aryl, alkylaryl or arylalkyl group, n=1, 2 or 3; k=0, 1 or 2; l=0 or 1, and x=a whole number having a maximum value corresponding to the number of double bonds in the compound B', and/or which is equal to the number of double bonds in the compound B' if l=1 and A is NHC(O)O or NHC(O)NR'.

Such silanes are described in German Patent Document DE 40 11 044 and in European Patent document 91 105 355.

The alkyl groups are, e.g., straight chain, branched or cyclic groups with from 1 to 20 carbon atoms, advantageously from 1 to 10 carbon atoms, and especially preferably lower alkyl groups having from 1 to 6 carbon atoms. Special examples include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with 2 to 20 carbon atoms, advantageously from 2 to 10 carbon atoms, and especially preferably lower alkenyl groups from 2 to 6 carbon atoms, such as vinyl, allyl or 2-butenyl groups.

The aryl groups are advantageously phenyl, biphenyl and naphthyl.

The alkoxy-, acyloxy-, alkylcarbonyl-, alkoxycarbonyl- and amino groups are advantageously derived by reaction from the above-described alkyl- and aryl groups. Special examples include methoxy, ethoxy, n- and i-propoxy, n, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-mentioned groups can of course have one or more substituents, as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxyl, mercapto, cyano, nitro, epoxy, $SO_3H$ and $PO_4H_2$.

The halogens are advantageously fluorine, chlorine and bromine.

The B group can be derived from a substituted or unsubstituted compound B' with at least two C=C double bonds, e.g. vinyl, allyl, acryl and/or methacrylate groups, and from 5 to 50, advantageously 6 to 30, carbon atoms. Preferably B is derived from a substituted or unsubstituted compound B' with two or more acrylate or methacrylate groups (compounds of this type are designated in the following as (meth)acrylate).

In case the compound B' is substituted, the substituents can be selected from the above-mentioned substituents.

The silanes according to the invention need not be isolated for preparation of the poly(heero)condensates. It is also possible to make these silanes first in a dropwise method and then condense hydrolytically—after addition of any additional hydrolyzable compounds which are needed.

The silicon compounds which can be used as hydrolytically condensable silicon compounds include the silicon compounds of the formula VIII $$Y_nSiX_mR_{4-(n+m)} \quad (VIII)$$

in an uncondensed or precondensed form.

The groups R, X and Y can be the same or different and have the following significance:

X represents hydrogen, halogen, a hydroxy group, an alkoxy group, an acyloxy group, an alkylcarbonyl group, an alkoxycarbonyl group and —NR'$_2$, where R' represents hydrogen, an alkyl group or an aryl group;

R represents an alkyl, alkenyl, aryl, alkylaryl or arylalkyl group,

Y is a substituted or unsubstituted 1, 4, 6-trioxaspiro-[4,4]-nonyl group; and n=1, 2 or 3, and m=1, 2 or 3, with n+m necessarily $\leq 4$.

These spiro-silanes are hydrolyzable via the X group and are polymerizable via the Y group and they are described in the German Patent Document 4125201 C1.

The alkyl groups are, e.g., straight chain, branched or cyclic groups with from 1 to 20 carbon atoms, advantageously from 1 to 10 carbon atoms, and especially preferably lower alkyl groups having from 1 to 6 carbon atoms. Special examples include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with 2 to 20 carbon atoms, advantageously from 2 to 10 carbon atoms, and especially preferably lower alkenyl groups from 2 to 6 carbon atoms, such as vinyl, allyl or 2-butenyl groups.

The aryl groups are advantageously phenyl, biphenyl and naphthyl.

The alkoxy-, acyloxy-, alkylcarbonyl-, alkoxycarbonyl- and amino groups are advantageously derived by reaction from the above-described alkyl- and aryl groups. Special examples include methoxy, ethoxy, n- and i-propoxy, n, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-mentioned groups can of course have one or more substituents, as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxyl, mercapto, cyano, nitro, epoxy, $SO_3H$ and $PO_4H_2$.

The halogens are advantageously fluorine, chlorine and bromine.

Additional hydrolytically condensable compounds which can be hydrolytically condensed with the hydrolytically condensable silicon compounds described above include the additional hydrolyzable aluminum-containing compounds of the formula $AlR^o{}_3$ in an uncondensed or precondensed form, in which $R^o$ is a halogen, hydroxy, an alkoxy or an acryloxy group. The alkoxy and acryloxy groups are advantageously defined in more detail in the same way as those same groups are defined in connection with the appropriate hydrolyzable silicon compounds described hereinabove. The above-mentioned groups can also be replaced completely or partially by chelate ligands (e.g. acetylacetone or acetoacetic acid, acetic acid).

Aluminum alkoxides and aluminum halides are particularly preferred as these additional hydrolyzable aluminum-containing compounds. Concrete examples of these compounds include the following:

$Al(OCH_3)_3$, $Al(OC_2H_5)_3$, $Al(O—n—C_3H_7)_3$, $Al(O—i—C_3H_7)_3$, $Al(OC_4H_9)_3$, $Al(O—i—C_4H_9)_3$, $Al(O—s—C_4H_9)_3$, $AlCl_3$, $AlCl(OH)_2$.

The additional hydrolyzable aluminum-containing compounds which are liquids at room temperature are particularly preferred, e.g. aluminum sec-butylate and aluminum isopropylate.

Additional hydrolytically condensable compounds which can be hydrolytically condensed with the hydrolytically condensable silicon compounds described above include the additional hydrolyzable titanium or zirconium-containing compounds of the formula $MX_yR_z$ in an uncondensed or precondensed form, in which y=1, 2, 3 or 4, especially y=2 to 4, and z=0, 1, 2 or 3, especially z=0,1, 2, and M is titanium or zirconium and X and R are as defined above in connection with the hydrolytically condensable silicon compounds of formula I. The y value of 4 is particularly preferred. The preferred X and R groups are also as defined above in connection with the compounds of formula I.

As is the case for the above-mentioned Al-containing compounds complexed Ti- or Zr-compounds can be used. Acrylic acid and methacrylic acid are additionally advantageous complex forming compounds. Similarly silanes according to the invention which have acryl- and/or methacryl groups, can also be used for complexing. In this case the advantage of using the silanes according to the invention having the acryl and/or methacryl groups is that no additional complexing agents are necessary for complexing the Ti and Zr-compounds.

Specific examples of the Zr- and Ti-compounds which can be used are as follows:

$TiCl_4$, $Ti(OC_2H_5)_4$, $Ti(OC_3H_7)_4$, $Ti(O—i—C_3H_7)_4$, $Ti(OC_4H_9)_4$, $Ti(2-ethylhexoxy)_4$, $ZrCl_4$, $Zr(OC_2H_5)_4$, $Zr(OC_3H_7)_4$, $Zr(O—i—C_3H_7)_4$, $Zr(OC_4H_9)_4$, $Zr(2-ethylhexoxy)_4$, $ZrOCl_2$.

Additional hydrolyzable compounds, which can be used for making polyheterocondensates, are, e.g., boron trihalides and boron acid esters, such as $BCl_3$, $B(OCH_3)_3$ and $B(OC_2H_5)_3$, tin tetrahalides and tin tetraalkoxides, such as $SnCl_4$ and $Sn(OCH_3)_4$, and vanadyl compounds, such as $VOCl_3$ and $VO(OCH_3)_3$.

As already mentioned, the making of the poly(hetero) condensates occurs in the standard way as in this field of the chemical arts. If silicon compounds are used exclusively, the hydrolytic condensation can occur generally so that the silicon compounds to be hydrolyzed, which are present either as such or dissolved in a suitable solvent, are added directly to the required amount of water at room temperature or under mild cooling (advantageously with stirring and in the presence of a hydrolysis and condensation catalyst) and the resulting mixture is stirred for a certain time interval (from one to several hours).

A stepwise addition of water is usually recommended in the presence of reactive compounds of Al, Ti or Zr. The hydrolysis generally takes place at temperatures of between $-20°$ to $130°$ C. advantageously from $0°$ to $30°$ C. and/or the boiling point of the required solvent independently of the reactivity of the compounds present. As already indicated, the best manner of adding the water depends above all on the reactivity of the starting materials being used. Thus for example the dissolved starting materials can be added slowly dropwise until present in excess with respect to the water or the water can be added in one portion or a plurality of portions to the starting materials. It can also be useful not to add the water as such to the starting materials, but instead to introduce it in situ in the reaction system with the help of a water-containing organic or inorganic system. In many cases the introduction of water in the reaction mixture with the help of moisture-laden absorbents, e.g. molecular sieves, and by water-containing organic solvents, e.g. 80% ethanol, has proven to be especially suitable. The required water addition can be provided by a chemical reaction in which water is released in the course of the reaction. For example esterification reactions would be suitable to produce the necessary water.

When a solvent is used, besides the lower aliphatic alcohols (e.g. ethanol or i-propanol), also ketones, advantageously lower dialkyl ketones, such as acetones or methyl iosbutyl ketones, ether, advantageously lower dialkyl ethers such as diethyl ether or dibutyl ether, THF, amides, esters, particularly acetic acid ester, dimethylformamide, amines, especially triethylamine, and their mixtures are also suitable for use as the solvent.

If spiro-silanes are used for making the poly(hetero) condensates, the hydrolysis is advantageously performed in a medium which is basic with respect to the spiro-silanes. This is provided either by a basic solvent, such as by triethylamine, or by addition of basic hydrolysis and condensation catalysts, such as $NH_3$, NaOH, KOH, Methyl imidazole, etc.

The starting materials need not all be present at the beginning of the hydrolysis(polycondensation), but in certain cases it has proven advantageous when only a part of the compounds are first brought into contact with water and then later the remainder of the compounds are added.

To avoid as much as possible precipitation during the hydrolysis and the polycondensation, particularly when using silicon compounds which hydrolyze to different extents, the water can be added in several stages, e.g. in three stages. In the first stage, e.g., from a tenth to a twentieth of the amount of water required for hydrolysis is added. After briefly stirring, the addition of from a fifth to a tenth of the required water can occur and, after another short time interval, the remainder of the water can be finally added.

The condensation time varies according to the starting components and their amounts, the necessary catalysts, the reaction temperatures, etc. Generally the polycondensation is performed at normal pressure, but it can also occur at elevated or reduced pressure.

The poly(hetero)condensate so obtained can either be further processed as such or with the solvent partially or completely removed. In some cases it has proven advantageous to replace the excess water and the solvent together with any optional additional solvent in the product obtained by polycondensation by another solvent to stabilize the poly(hetero)condensate. The reaction mixture can be further concentrated for this purpose, e.g., in vacuo at a gently elevated temperature, so that the reaction mixture can be received in another solvent without additional problems.

If these poly(hetero)condensates are used as paints for coatings (e.g. of plastic materials such as PVC, PC, PMMA, PE, PS, etc, of glass, paper, wood, ceramics, metal, etc), conventional paint additives can be added, at the latest immediately prior to use. These conventional paint additives include, e.g., coloring agents (pigments or dyes), filling materials, antioxidants, fire retardants, thinning agents, UV-absorbers, stabilizers or the like. Also additives for increasing the electrical conductivity (e.g. graphite powder, silver powder, etc) can be mentioned in this connection. Inorganic and/or organic filling materials, such as organic and inorganic particles, (glass) fibers, minerals, etc., can be added when the poly(hetero)condensates are used to make molded bodies.

The final hardening of the poly(hetero)condensates occurs after addition of suitable initiators thermally, in a redox induced manner, covalent-nucleophilically or photochemically. Several hardening mechanisms can proceed in parallel or in succession. Thus the C=C double bonds are coupled in the course of polymerization and an organic network is built up. Because of the comparatively high molecular weight of the silanes according to the invention only a reduced volume shrinkage occurs during the hardening.

It is also possible to add additional ionically and/or radically polymerizable components to the poly(hetero) condensate prior to the final hardening, also prior to the polymerization. Radically polymerizable compounds, which can be used, are, e.g., those with C=C double bonds such as acrylates or methacrylates in which polymerization can occur at the C=C double bond. Ionically polymerizable compounds, which can be added, contain, e.g., ring systems, which are polymerizable by cationic ring opening. These ionically polymerizable compounds can include spiroorthoesters, spiroorthocarbonates, bicyclic spiroorthoesters, mono- or oliogoepoxides or spirosilanes of the general formula VIII above. However compounds can also be added, which are both ionically and radically polymerizable, such as, e.g., methacryloyl spiroorthoesters. These are radically polymerizable via the C=C double bond and cationically polymerizable via ring opening. These systems are, described, e.g., in Journal f. prakt. Chemie (Journal for Practical Chemistry), Volume 330, Number 2, 1988, pp. 316–318 or in the Journal of Polymer Science: Part C: Polymer Letters, Vol. 26, pp. 517–520(1988).

If the hardening of the poly(hetero)condensates occurs photochemically, then photoinitiators are added; but if the hardening occurs thermally, thermal initiators are added. In redox-induced hardening starter-activator systems are added.

The initiator can be added in the standard amount. Thus, e.g., a mixture, which contains 30 to 50% by weight of solid polycondensate and initiators in the amount of from 0.5 to 5% by weight for example, advantageously 1 to 3% by weight, in relation to the total amount of mixture can be added.

If additional components besides the silanes are used to make the poly(hetero)condensates, which contain reactive double bonds, e.g. silanes according to the formula VII, thus a polymerization can occur via these double bonds, which can be thermally and/or photochemically and/or covalent-nucleophilically and/or redox initiated.

Commercially obtained photoinitiators can be used. For example, Iracure 184 (1-hydroxycyclohexylphenylketone), Irgacure 500 (1-hydroxycyclohexylphenylketone/benzophenone) and other photoinitiators obtained from Ciba Geigy; Darocure 1173, 1116, 1398, 1174 and 1020 (obtained from Merck); benzophenone, 2-chlorothioxanthone, 2-methylthioxanthone, 2-isopropylthioxanthone, benzoin, 4,4'-dimethylbenzoin, etc. can be used as the commerical photoinitiator. If the hardening occurs by visible light, e.g. in the dental field, campherchionon can be used as the photoinitiator.

Especially organic peroxides in the form of diacyl peroxides, peroxydicarbonates, alkyl peresters, dialkyl peroxides, perketals, ketone peroxides and alkyl hydroperoxides can be used as thermal initiators. Specific and advantageous examples of thermal initiators include dibenzyl peroxide, t-butyl perbenzoate and azobisisobutyronitrile.

Standard starter/activator systems can generally be used. For example aromatic amines (e.g. N,N-bis-(2-hydroxyethyl)-p-toluidine) can be used as activator and dibenzoyl peroxide can be used as starter. The hardening time can be adjusted by changing the concentration or concentration ratios of starter and activator. Additional amines for this purpose are, e.g., described in German Patent Document DE 4310733.

For example initiators with at least one amino group can be used in covalent-nucleophilic hardening. Suitable amines, for example, are described in German Patent Document DE 4405261.

A paint (poly(hetero)condensates) based on the silanes of the invention and provided with an intiator can be used to provide a coating on a substrate. Standard coating methods can be used to apply the coating to the substrate. These coating methods include, e.g., dipping, flooding, pouring, centrifuging, rolling, spraying, brushing on, electrostatic spraying and electronic immersion painting. It should also be noted that the paint does not necessarily need to contain a solvent. Particularly when silanes with two alkoxy groups at the Si atom are used as starting materials to make the condensate it is not necessary to add a solvent.

The applied paint may advantageously be dried prior to hardening. After that it can be hardened in a known manner according to the type of initiators: redox-induced, thermal or photochemical. Understandably also combinations of hardening methods are also possible.

When the hardening of the applied paint occurs by irradiation, it has proven advantageous, after the hardening by irradiation, to perform a thermal hardening, particularly to remove the solvent still present or to include other reactive groups in the hardening.

Although polymerizable groups are already present in the poly(hetero)condensates because they are based on the silanes according to the invention, it can prove advantageous in certain cases to add still more compounds with unsaturated double bonds (advantageously pure organic compounds) to these condensates prior to or in further processing (hardening). Acrylic acid and methacrylic acid and compounds derived from them, especially esters of advantageously single functional alcohols (e.g. $C_{1-4}$ alcohols), (meth)acrylonitrile, styrol and mixtures of the foregoing are advantageous examples. These other added compounds can simultaneously act as solvents and/or thining agents in the case of the poly(hetero)condensates.

The manufacture of molded bodies and/or castings from poly(heto)condensates based on the silanes according to the invention can take place in accordance with any of the methods currently available in this field, e.g. by pressing, casting, injection molding, extrusion, etc. Poly(hetero) condensates based on the silanes according to the invention are also suitable for making composite materials (e.g. with fiber glass reinforcement).

The making of hydrolytically condensable polymerizates is another possible application of the silanes according to the invention. The silanes according to the invention are furthermore polymerizable alone or together with other radically and/or ionically polymerizable components. The final hardening can then occur by hydrolytic condensation via the hydrolyzable groups of the silanes according to the invention and eventually also the other hydrolyzable components. In this case the organic network is built up first by polymerization and then the inorganic network is built up by hydrolytic condensation.

The making of the polymerizates according to the invention occurs by radical and/or ionic polymerization of one or more C=C double bond-containing compounds and other radically and/or ionically polymerizable compounds as needed. The polymerization can be redox-induced and/or covalent-nucleophilic and/or by action of heat and/or electromagnetic radiation, as needed in the presence of one or more initiators and/or a solvent. The polymerizates include from 5 to 100 Mol percent, based on the monomer compounds, of the C=C double bond-containing compounds from the silanes according to the invention of formula I.

It is also possible to add additional ionically and/or radically polymerizable components to the silanes according to the invention prior to the polymerization. Radically polymerizable compounds, which can be added, are for examples compounds with C=C double bonds, such as acrylate or methacrylate. The polymerization of these compounds occurs via the C=C double bonds. Ionically polymerizable comounds, which can be added, contain e.g. ring systems, which are polymerizable by cationic ring opening, such as spiroorthoesters, spiroorthocarbonates, bicyclic spiroorthoesters, mono- or oligoepoxides or spiro-silanes of the formula VIII. However compounds can also be added, which are both ionically and radically polymerizable, such as, e.g., methacryloyl spiroorthoesters. These are radically polymerizable via the C=C double bond and cationically polymerizable via ring opening. These systems are, described, e.g., in Journal f. prakt. Chemie (Journal for Practical Chemistry), Volume 330, Number 2, 1988, pp. 316–318 or in the Journal of Polymer Science: Part C: Polymer Letters, Vol. 26, pp. 517–520(1988).

Furthermore additional hydrolyzable and polymerizable silicon compounds can be added to the silanes according to the invention prior to polymerization, if necessary in precondensed form, which then can be copolymerized. These additional silicon compounds are derived, e.g., from epoxide-containing silanes, are thus cationically polymerizable and are used, among other things, for making the spiro-silanes according to German Patent Document DE 4125201 C1. These systems are described in German Patent Document DE 4125201 C1.

Silicon compounds which are derived from those of formula VII and are radically polymerizable can also be used as the silicon compounds. These systems have already been described in detail in connection with the production of the poly(hetero)condensates.

The polymerization occurs by a covalent-nucleophilic and/or redox-induced and/or thermal and/or photochemical mechanism after addition of a suitable initiator. Thus C=C double bonds are coupled , e.g., in a single step radical polymerization, and ring opening of spiro group rings and, as needed, additional rings occurs in a single cationic polymerization. Because of that the organic network is built up. Surprisingly it was found that in the course of these polymerizations the volume of the reaction mass does not change or changes only slightly. The comparatively high molecular weight of the silanes according to the invention is responsible for that.

If the polymerization occurs photochemically, photoinitiators are added to the reaction mass. If the polymerization occurs thermally, thermal initiators are added. If the polymerization is redox induced, starter/activator systems are added.

If components with spiro groups are added to the silanes according to the invention, a polymerization can occur because of these components which is thermally or photochemically initiated. Photoinitiators obtained commercially can be used for this purpose.

The initiator can be added in the standard amount. Thus, e.g., a mixture, which contains 30 to 50% by weight of solid polycondensate and initiators in the amount of from 0.5 to 5% by weight for example, advantageously 1 to 3% by weight, in relation to the total amount of mixture can be added.

The polymerizate obtained in this way can be hydrolytically condensed, if necessary, in the presence of additional hydrolytically condensable silicon compounds and, if necessary, other elements from the group consisting of B, Al, P, Sn, Pb, transition metals, lanthanide metals and actinide metals, in uncondensed or precondensed from, with water or moisture, if necessary in the presence of a catalyst and/or solvent, to form an inorganic network. The polymerizate contains hydrolyzable groups X, e.g. alkoxy groups, so that an inorganic network (Si—O—Si bonds) can be built up.

The hydrolyzable silicon compounds of formula VI, if necessary in precondensed form, are particularly preferred. These systems were already described in detail in connection with the preparation of the poly(hetero)condensates and illustrated with concrete examples.

Those hydrolyzable aluminum-containing compounds used for the above purpose that are particularly preferred include those of the formula $AlR^o{}_3$ and suitable Titanium or Zirconium compounds, which may be used as needed for the above purpose are those of the formula $MX_yR_z$. Also these systems are already handled in detail in connection with the preparation of poly(hetero)condensates.

Additional hydrolyzable compounds, which can be added to the polymerizate, are, e.g., boron trihalides and boron acid esters, such as, e.g., $BCl_3$, $B(OCH_3)_3$ and $B(OC_2H_5)_3$, tin tetrahalides and tin tetraalkoxides, e.g. $VOCl_3$ and $VO(OCH_3)_3$.

The hydrolytic condensations, as already mentioned, can occur in the manner which is usual in this field of the chemical arts. The hydrolytic condensation can occur in most cases so that the required water is added directly with mild cooling or at room temperature to the polymerizate to be hydrolyzed, either as such or dissolved in a suitable solvent, advantageously with stirring and in the presence of a hydrolysis and condensation catalyst.

A stepwise addition of water is recommended in the presence of reactive compounds of Al, Ti or Zr. The hydrolysis generally takes place at temperatures of between −20° to 130° C., advantageously from 0° to 30° C., and/or the boiling point of the required solvent independently of the reactivity of the compounds present. As already indicated, the best manner of adding the water depends above all on the reactivity of the starting materials being used. Thus for example the dissolved starting materials can be added slowly dropwise until present in excess with respect to the water or the water can be added in one portion or a plurality of portions to the starting materials. It can also be useful not to add the water as such to the starting materials, but instead to introduce it in situ in the reaction system with the help of a water-containing organic or inorganic system.

The production of new inorganic-organic polymer compounds with widely variable properties and/or modification of existing polymer compounds is possible with the reactant compounds made available with the multifunctional silanes according to the invention. This type of material can be used in a wide variety of applications including, among others, those related to bulk materials, composites, adhesive materials, castings, coating materials, adhesive materials and binding agents for ceramic particles (ceramic casting processes), making and/or priming of filling materials and fibers, of grinding wheels, reaction extruders, etc. The organic polymerization can occur by a photochemical, thermal or chemically (2-components, anaerobic, Redox, etc.) induced mechanism.

The invention is illustrated in more detail without limitation by the following examples.

EXAMPLES

Example 1

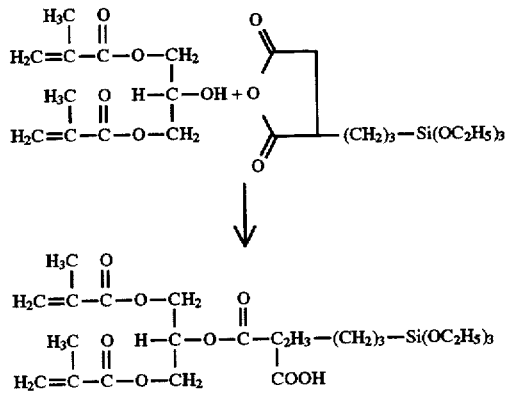

The reactants, 12.7 g (0.05 mol) glycerin-1,3-dimethacrylate, are added dropwise under dry atmosphere to 17.0 g (0.05 mol) triethoxysilylpropylsuccinic anhydride. The reaction can be followed by monitoring the anhydride carbonyl bands ($v_{as(C=O)}$=1786 cm$^{-1}$, $v_{sy(C=O)}$=1864 cm$^{-1}$). Since a catalyst and/or solvent must not be added, the desired product (liquid) is obtained after completing the reaction and can be used without further purification.

| IR Data: | |
|---|---|
| $v_{(OH \leftrightarrow COOH)}$ = | 3450–2500 cm$^{-1}$ |
| $v_{(C=O \leftrightarrow methacryl/ester/COOH)}$ = | 1726 cm$^{-1}$ |
| $v_{(C=C \leftrightarrow methacryl)}$ = | 1638 cm$^{-1}$ |

Example 2

Hydrolysis and Condensation of the Product of Example 1

A solution of 53.5 g (0.1 mol) product from Example 1 in 100 ml of ethyl acetate is mixed and stirred with 4.4 g water (self-catalyzed by the acid group and/or with added catalyst) for hydrolysis and condensation of the ethoxy groups. After completion of the transformation (detected by H$_2$O titration) the resulting solution, e.g., can be used for coating (with subsequent hardening, i.e. polymerization of the methacryl groups) a variety of substrates.

Example 3

Complexing of Zr(OPr)$_4$ with the Carboxyl Groups of the Product of Example 1

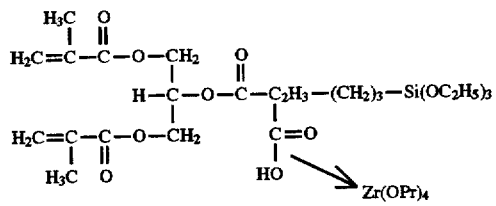

16.0 g (37.5 mmol) of zirconium isopropylate (Zr(OPr)$_4$) are added dropwise to 20.0 g (37.5 mmol) of the product of example 1. The complexing can be followed by monitoring the decrease of the $v_{(OH \rightleftharpoons COOH)}$ band at 3450 to 2500 cm$^{-1}$ and the increase of the Zr-carbonyl complex bands at 1450 to 1600 cm$^{-1}$. The resulting clear liquid can be used directly in further reactions or the split off i-propanol can be drawn off for further characterization.

IR Data:

| | |
|---|---|
| $v_{(CH \rightarrow aliphat.)} =$ | 2970–2800 cm$^{-1}$ |
| $v_{(C=O \rightarrow methacryl/ester)} =$ | 1727 cm$^{-1}$ |
| $v_{(C=C \rightarrow complex)} =$ | 1450–1600 cm$^{-1}$ |

Example 4

Hydrolysis and Condensation of the Product of Example 3

The propanol-containing solution from Example 3 (37.5 mmol zirconium complex) is mixed and stirred with 2.7 g water (including catalyst) after addition of 2.5 g (7.5 mmol) 1,12-dodecanedioldimethacrylate for hydrolysis and condensation of the ethoxy- and/or propoxy groups. After completing the reaction (detected by H$_2$O titration) the solution, e.g., can be used for coating of various substrates (with subsequent hardening, i.e. polymerization of the methacrylate groups).

Example 5

Hydrolysis and Condensation of the Product of Example 3

The propanol-containing solution from Example 3 is mixed and stirred with 7.1 g of water (including catalyst) after addition of 200 ml ethyl acetate for hydrolysis and condensation of the ethoxy and/or propoxy groups. After a few hours (detected by H$_2$O titration) the solution can be used, e.g., for coating of various substrates (with subsequent hardening, i.e. polymerization of the methacrylate groups).

Example 6

Binding of (C$_4$H$_9$)$_2$Sn(OCH$_3$)$_2$ to the Carboxyl Groups of the Product of Example 1

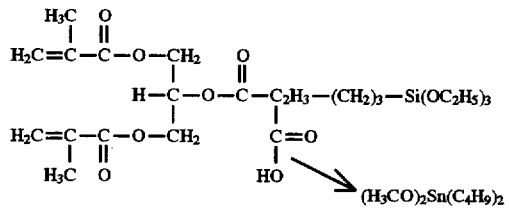

50 g (17.0 mmol) dibutyltindimethylate were added dropwise to 9.1 g (17.0 mmol) of the product of Example 1 under a dry atmosphere. The binding reaction can be followed by monitoring the decrease of the $v_{(OH \rightleftharpoons COOH)}$ band at 3450 to 2500 cm$^{-1}$ and the increase of the Sn-carbonyl complex bands at 1450 to 1630 cm$^{-1}$. The resulting clear liquid can be used directly in further reactions or the split off methanol can be drawn off for further characterization.

IR Data:

| | |
|---|---|
| $v_{(CH \rightarrow aliphat.)} =$ | 2970–2800 cm$^{-1}$ |
| $v_{(C=O \rightarrow methacryl/ester)} =$ | 1727 cm$^{-1}$ |
| $v_{(C=O/O=C \rightarrow complex)} =$ | 1450–1600 cm$^{-1}$ |

Example 7

Hydrolysis and Condensation of the Product of Example 3 in combination with Another Methacrylate Silane

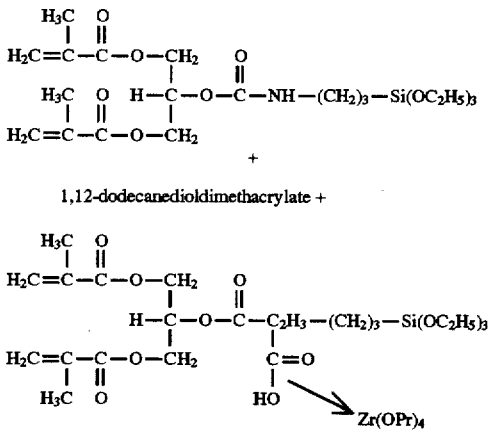

23.3 g (0.1 mol) glycerin-1,3-dimethacrylate and dibutyltindilaurate (as additional catalyst) are added dropwise at room temperature under dry air to 25.3 g (0.1 mol) 3-isocyanatopropyltriethoxysilane. After about two hours stirring the addition is complete(as determined by IR control). The resulting reaction mixture is mixed with 6.9 g (20 mmol) 1,12-dodecanedioldimethacrylate, 100 ml ethyl acetate and the propanol-containing solution from Example 3 (40 mmol zirconium complex). The resulting mixture is mixed and stirred with 7.4 g water (including catalyst) for hydrolysis and condensation of the ethoxy and propoxy groups. After the transformation is complete (detected by H$_2$O titration), the solution can be used immediately to coat a variety of substrates (with subsequent hardening, i.e. polymerization of the methacrylate groups). To obtain a solvent-free resin, e.g. for mold body formation, the above-mentioned solution is shaken with water, filtered, rotated and completely freed of volatile components with an oil pump. The clear nearly colorless resin is obtained with a yield of about 96% and can be used for the following hardening (Example 8).

Example 8

Making of a Sample Body for determination of Mechanical and Thermal Data

1% Irgacure (UV-Initiator of Ciba Geigy) is dissolved in 12 g of resin from Example 7 and the mixture is formed into a rod-shaped body (2×2×25 mm). The double bonds are reacted via a UV-induced radical polymerization. Furthermore both sides are each irradiated 100 seconds with a UV-point source of radiation. The E-modulus and the breaking strength of the resulting rod are determined by 3-point bending experiments. The thermal expansion coefficient α is determined in a temperature range of from 5° to 50° C. with a dilatometer. The results for the properties measured are as follows:

E-modulus=2840 MPa (±100);
α=76×10⁻⁶ K⁻¹
Strength $\sigma_B$=93 MPa (±10)

Example 9

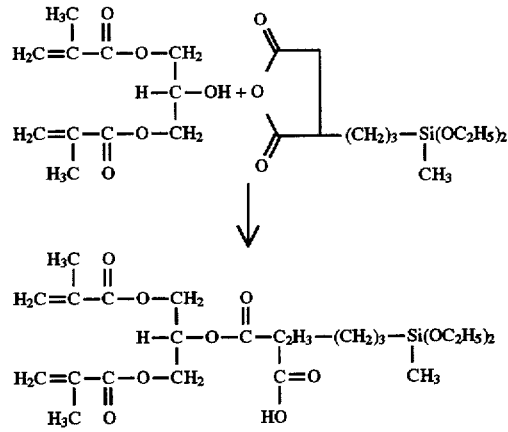

4.6 g (20 mmol) glycerin-1,3-dimethacrylate are added dropwise under a dry atmosphere to 5.5 g (20 mmol) 3-(methyldiethoxysilyl)-propylsuccinic anhydride. The reaction can be followed by monitoring the decrease of the anhydride carbonyl bands ($v_{as(C=O)}$=1786 cm⁻¹, $v_{sy(C=O)}$ =1864 cm⁻¹). Since a catalyst and/or solvent must not be added, the desired product (liquid) is obtained after completing the reaction and can be used without further purification.

| IR Data: | |
|---|---|
| $v_{(OH \leftrightarrow COOH)}$ = | 3500–2500 cm⁻¹ |
| $v_{(C=O \leftrightarrow methacryl/ester/COOH)}$ = | 1725 cm⁻¹ |
| $v_{(C=C \leftrightarrow methacryl)}$ = | 1638 cm⁻¹ |

Example 10

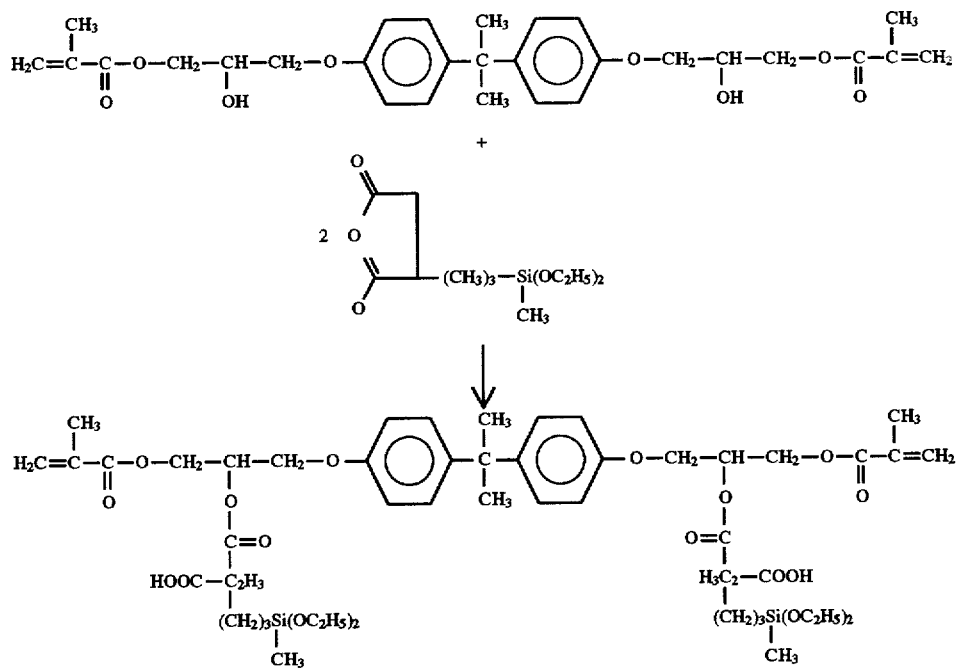

10.3 g (20 mmol) of 2,2-bis-[p-(2-hydroxy-3-methacryloyloxypropoxyl)phenyl]propane in 20 ml of THF is added dropwise to 11.0 g (40 mmol) of 3-(methyldiethyoxysilyl)propylsuccinic acid anhydride. The reaction can be followed by monitoring the decrease of the anhydride carbonyl bands ($v_{as(C=O)}$=1786 cm$^{-1}$, $v_{sy(C=O)}$=1864 cm$^{-1}$). Since a catalyst and/or solvent must not be added, the desired product (liquid) is obtained after completing the reaction and can be used without further purification.

IR Data:

| | |
|---|---|
| $v_{(OH \leftarrow\rightarrow COOH)}$ = | 3430–2400 cm$^{-1}$ |
| $v_{(C=O \leftarrow\rightarrow methacryl/ester/COOH)}$ = | 1724 cm$^{-1}$ |
| $v_{(C=C \leftarrow\rightarrow methacryl)}$ = | 1638 cm$^{-1}$ |

Example 11

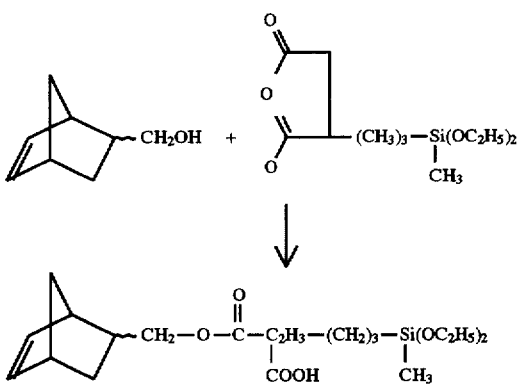

2.48 g (20 mmol) 2-hydroxymethyl-5-norbornene are added dropwise to 5.5 g (20 mmol) 3-(methyldiethoxysilyl)propylsuccinic acid anhydride under a dry atmosphere. The reaction can be followed by monitoring the decrease of the anhydride carbonyl bands ($v_{as(C=O)}$=1786 cm$^{-1}$, $v_{sy(C=O)}$=1864 cm$^{-1}$). Since a catalyst and/or solvent must not be added, the desired product (liquid) is obtained after completing the reaction and can be used without further purification.

IR Data:

| | |
|---|---|
| $v_{OH \leftarrow\rightarrow COOH}$ = | 3400–2400 cm$^{-1}$ |
| $v_{(C=O \leftarrow\rightarrow ester/COOH)}$ = | 1736/1711 cm$^{-1}$ |
| $v_{(CH \leftarrow\rightarrow olefin)}$ = | 3059 cm$^{-1}$ |

Example 12

Hydrolysis and Condensation of the Product of Example 11

The solution of 8.0 g (20 mmol) of product of Example 11 in 40 ml of ethyl acetate is mixed and stirred with 0.58 g water (self-catalyzed by acid groups and/or with added catalyst) to hydrolyze and condense the ethoxy groups). After the reaction is complete (as detected by H$_2$O titration) the solution, e.g.. can be used to coat any substrate (with subsequent hardening , i.e. polymerization of the methacrylate groups). To obtain a solvent-free resin, e.g. for mold body manufacture, the above-mentioned solution is shaken with water, filtered, rotated and freed of the volatile components completely with an oil pump. The clear resin is obtained with a yield of about 96% and is used for hardening.

While the invention has been illustrated and described as embodied in hydrolyzable and polymerizable silanes, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

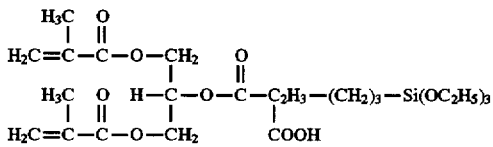

We claim:

1. A hydrolyzable and polymerizable silane of the formula I,

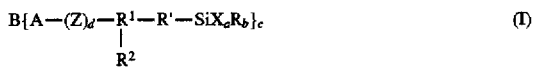

wherein
a=1, 2 or 3,
b=0, 1 or 2,
with the proviso that a+b necessarily=3; and
c=1, 2, 3 or 4;
wherein
B=a straight chain or branched organic residue having at least one C=C double bond and having 4 to 50 carbon atoms;
X represents a member selected from the group consisting of hydrogen, halogen, hydroxy groups, alkoxy groups, acyloxy groups, alkylcarbonyl groups, alkoxycarbonyl groups and —NR"$_2$;
R" represents a member selected from the group consisting of hydrogen, alkyl groups and aryl groups;
R represents a member selected from the group consisting of alkyl groups, alkenyl groups, aryl groups, alkylaryl groups and arylalkyl groups;
R' represents a member selected from the group consisting of substituted and unsubstituted alkylene groups, arylene groups, arylenealkylene groups and alkylene-arylene groups each having zero to ten carbon atoms, wherein said substituted alkylene groups, said substituted arylene groups, said substituted arylenealkylene groups and said substituted alkylenearylene groups each have at least one substituent selected from the group consisting of oxygen atoms, sulfur atoms and amine groups;
R$^1$ is a member of the group consisting of nitrogen, substituted and unsubstituted alkylene, arylene and alkylenearylene groups each having from 1 to 10 carbon atoms, wherein said substituted alkylene groups, said substituted arylene groups and said substituted alkylenearylene groups each having from 1 to 10 carbon atoms each have at least one substitutent selected from the group consisting of oxygen atoms, sulfur atoms and amine groups;
R$^2$ is a member selected from the group consisting of H, OH and COOH; and
wherein,
when said d=1, Z=CO, said R$^1$ is one of said substituted and unsubstituted alkylene groups, arylene groups and alkylenearylene groups each having from 1 to 10 carbon atoms and said $R^2$ is one of said H and said COOH, then A represents a member selected from the group consisting of an oxygen atom, a sulfur atom and an NH group; and wherein, when said d=1, Z=CHW and W represents a member selected from the group consisting of H, alkyl groups, aryl groups and alkyaryl groups, said $R^1$ is one of said substituted and unsubstituted alkylene groups, said arylene groups and said alkylenearylene groups each having from 1 to 10 carbon atoms and said $R^2$ is said OH, then A represents a member selected from the group consisting of an oxygen atom, a sulfur atom, an NH group and a COO group; and wherein, when said d=0 and said $R^1$ is one of said substituted and unsubstituted alkylene groups, arylene groups and alkylenearylene groups having from 1 to 10 carbon atoms and said $R^2$ is said OH, then A represents a member selected from the group consisting of an oxygen atom, a sulfur atom, an NH group and a COO group; and wherein, when said d=1, Z=CO, said $R^1$ is said nitrogen and said $R^2$=said H, then A is S.

2. A hydrolyzable and polymerizable silane as defined in claim 1, wherein said X is one of said halogen and said alkoxy groups, with the proviso that said alkoxy groups have from one to four carbon atoms, said R is one of said alkyl groups, with the proviso that said alkyl groups have from one to four carbon atoms, and said R' is one of said alkylene groups, with the proviso that said alkylene groups have from one to four carbon atoms.

3. A hydrolyzable and polymerizable silane as defined in claim 2, wherein said halogen is chlorine.

4. A hydrolyzable and polymerizable silane as defined in claim 2, wherein said X is selected from the group consisting of methoxy and ethoxy.

5. A hydrolyzable and polymerizable silane as defined in claim 2, wherein said R is selected from the group consisting of methyl and ethyl.

6. A hydrolyzable and polymerizable silane as defined in claim 2, wherein said R' is selected from the group consisting of methylene, ethylene and propylene.

7. A hydrolyzable and polymerizable silane as defined in claim 1, wherein said B includes at least one member selected from the group consisting of an acrylate group and a methacrylate group.

8. A hydrolyzable and polymerizable silane as defined in claim 1, wherein said B is derived from a member of the group consisting of acrylic acid esters of trimethylolpropane, pentaerythritol, dipentaerythritol, alkanediols having two to four carbon atoms, polyethylene glycols, polypropylene glycols and unsubstituted and substituted and alkyoxylated bisphenol A.

9. A process for making a hydrolyzable and polymerizable silane of the formula I as defined in claim 1 comprising performing an addition reaction of $B(AH)_c$ to a cyclic carboxylic acid anhydride of the formula II

and wherein said $R^1$ is one of said alkylene groups, said arylene groups and said alkylarylene groups, said A is one of said oxygen atom, said sulfur atom and said NH group, and said B, R, a, b, a+b, c and X are as defined in claim 1.

10. A process for making a hydrolyzable and polymerizable silane of the formula I as defined in claim 1 comprising performing a condensation reaction of $B(AH)_c$ with a carboxylic acid derivative of the formula III

wherein Y is selected from the group consisting of Cl, OH and OR* wherein R* and said $R^1$ are each independently one of said alkylene groups and said alkylenearylene groups, said A is one of said oxygen atom, said sulfur atom and said NH group, and said B, R, R', a, b, a+b, c and X are as defined in claim 1.

11. A process for making a hydrolyzable and polymerizable silane as defined in claim 1 comprising performing an addition reaction of $B(AH)_c$ to a substituted epoxide selected from the group consisting of epoxides of formula IV and epoxides of formula IX:

and said A is one of said oxygen atom, said sulfur atom, said NH group and said COO group, and said B, X, R, R', a, b, a+b and c are as defined in claim 1.

12. A process for making a hydrolyzable and polymerizable silane of the formula I as defined in claim 1, said process comprising performing an addition reaction, said additional reaction including adding $B(AH)_c$ to a substituted silane of formula V

wherein said A is a sulfur atom and said B, X, R, R', a, b, a+b and c are as defined in claim 1.

13. A hydrolyzable and polymerizable silane selected from the group consisting of silanes of the formula X and silanes of the formula XI:

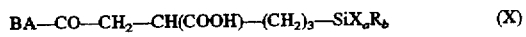

and

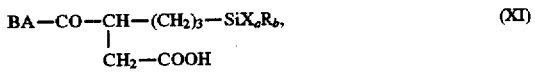

wherein a=1, 2 or 3;

b=0, 1 or 2;

with the proviso that a+b necessarily=3;

wherein

B=a straight chain or branched chain organic residue having at least one C=C double bond and having 4 to 50 carbon atoms;

wherein

A is a member selected from the group consisting of —O—, —S— and —NH—;

X represents a member selected from the group consisting of hydrogen, halogen, hydroxy groups, alkoxy groups, acyloxy groups, alkylcarbonyl groups, alkoxycarbonyl groups and —NR"$_2$;

R" represents a member selected from the group consisting of hydrogen, alkyl groups and aryl groups;

R represents a member selected from the group consisting of alkyl groups, alkenyl groups, aryl groups, alkylaryl groups and arylalkyl groups.

14. A hydrolyzable and polymerizable silane selected from the group consisting of silanes of the formula X, silanes of the formula XI, silanes of formula XII, silanes of formula XIII, silanes of formula XIV, silanes of formula XV, silanes of formula XVI and silanes of the formula XVII:

$$BA-CO-CH_2-CH(COOH)-(CH_2)_3-SiX_aR_b \quad (X)$$

$$BA-CO-\underset{CH_2-COOH}{\overset{|}{CH}}-(CH_2)_3-SiX_aR_b, \quad (XI)$$

$$BA-CO-(CH_2)_3-SiX_aR_b, \quad (XII)$$

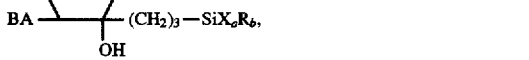  (XIII)

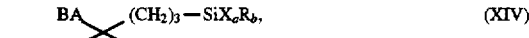  (XIV)

$$BA-CH(CH_3)-CHOH-CH_2-O-(CH_2)_3-SiX_aR_b, \quad (XV)$$

$$BA-\underset{CH_3-CH-OH}{\overset{|}{CH}}-CH_2-O-(CH_2)_3-SiX_aR_b, \quad (XVI)$$

$$BA-CO-NH-(CH_2)_3-SiX_aR_b, \quad (XVII)$$

wherein a, b, A, B, R and X are as defined in claim 1.

15. A hydrolyzable and polymerizable silane as defined in claim 14, wherein said X is chlorine.

16. A hydrolyzable and polymerizable silane as defined in claim 14, wherein said X is selected from the group consisting of methoxy and ethoxy.

17. A hydrolyzable and polymerizable silane as defined in claim 14, wherein said R is selected from the group consisting of methyl and ethyl.

18. A hydrolyzable and polymerizable silane as defined in claim 14, wherein said B includes at least one member selected from the group consisting of an acrylate group and a methacrylate group.

19. A hydrolyzable and polymerizable silane as defined in claim 14, wherein said B is derived from a member of the group consisting of acrylic acid esters of trimethylolpropane, pentaerythritol, dipentaerythritol, alkanediols having two to four carbon atoms, polyethylene glycols, polypropylene glycols and unsubstituted and substituted and alkyoxylated bisphenol A.

20. A hydrolyzable and polymerizable silane as defined in claim 13, wherein said a=3, said b=0, said A=—O— and said X=alkoxy.

21. The hydrolyable and polymerizable silane as defined in claim 20, and having the formula: